US012745895B2

(12) United States Patent
Mitsuhashi et al.

(10) Patent No.: US 12,745,895 B2
(45) Date of Patent: Sep. 29, 2026

(54) ENDOSCOPE PACKAGE SYSTEM, MANUFACTURING METHOD OF ENDOSCOPE, AND HOLDING BODY

(71) Applicant: OLYMPUS MEDICAL SYSTEMS CORP., Tokyo (JP)

(72) Inventors: Keita Mitsuhashi, Hachioji (JP); Wataru Matsuura, Fuchu (JP); Motohiko Suzuki, Sagamihara (JP); Takuto Yoshinaga, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 15 days.

(21) Appl. No.: 18/823,776

(22) Filed: Sep. 4, 2024

(65) Prior Publication Data

US 2025/0072728 A1 Mar. 6, 2025

Related U.S. Application Data

(60) Provisional application No. 63/536,740, filed on Sep. 6, 2023.

(51) Int. Cl.

| | |
|---|---|
| ***A61B 1/00*** | (2006.01) |
| ***B65B 5/04*** | (2006.01) |
| ***B65B 55/12*** | (2006.01) |

(52) U.S. Cl.

CPC ...... *A61B 1/00144* (2013.01); *A61B 1/00103* (2013.01); *A61B 1/00128* (2013.01); *B65B 5/04* (2013.01); *B65B 55/12* (2013.01)

(58) Field of Classification Search

CPC ............ A61B 1/00144; A61B 1/00103; A61B 1/00128; B65B 5/04; B65B 55/12

USPC .......................................................... 206/363

See application file for complete search history.

(56) References Cited

U.S. PATENT DOCUMENTS 3,633,758 A * 1/1972 Morse ................. A61M 25/002 211/85.13
4,925,448 A * 5/1990 Bazaral ............... A61M 25/002 206/370
5,031,775 A * 7/1991 Kane ...................... A61B 50/30 604/179
5,334,142 A * 8/1994 Paradis ............ A61B 17/12109 604/509

(Continued)

FOREIGN PATENT DOCUMENTS

JP 2002-045335 A 2/2002
JP 2002-533191 A 10/2002

(Continued)

*Primary Examiner* — Jacob K Ackun

(74) *Attorney, Agent, or Firm* — Morgan, Lewis & Bockius LLP

(57) ABSTRACT

In order to provide an endoscope that can reduce imbalance in shrinkage of an insertion portion and imbalance in slackening of bending wires even if a sterilization process involving heating is performed with respect to the endoscope stored in a container or the like while achieving the downsizing of a storage form used to store the endoscope in the container or the like, the endoscope package system includes an endoscope, the endoscope includes: a flexible insertion portion; in a length direction of the flexible insertion portion, the flexible insertion portion has a shape that includes a first winding direction and a second winding direction, the first winding direction is different from the second winding direction.

12 Claims, 16 Drawing Sheets

(56) References Cited

U.S. PATENT DOCUMENTS

| | | | | | |
|---|---|---|---|---|---|
| 5,526,928 | A * | 6/1996 | Yabe | A61B 1/121 206/363 | |
| 9,022,212 | B2 * | 5/2015 | Spaargaren | A61M 25/002 206/364 | |
| 9,220,400 | B2 | 12/2015 | Petersen | | |
| 2002/0015673 | A1 | 2/2002 | Moriyama | | |
| 2003/0192799 | A1 | 10/2003 | Addy et al. | | |
| 2005/0178684 | A1 * | 8/2005 | Kesler | A61M 25/002 206/364 | |
| 2006/0278546 | A1 * | 12/2006 | State | A61M 25/002 206/363 | |
| 2014/0262882 | A1 * | 9/2014 | Barnell | A61M 25/002 264/534 | |
| 2015/0068941 | A1 * | 3/2015 | Caron | A61M 25/002 206/364 | |
| 2016/0073862 | A1 * | 3/2016 | Matsuno | A61B 18/1492 206/370 | |
| 2019/0167078 | A1 * | 6/2019 | Fryer | A61B 1/00142 | |
| 2019/0167824 | A1 * | 6/2019 | Rhodes | A61B 1/00144 | |
| 2019/0262577 | A1 * | 8/2019 | Anderson | A61B 1/00144 | |
| 2023/0115558 | A1 * | 4/2023 | Ashizuka | A61B 1/018 600/104 | |
| 2023/0255451 | A1 * | 8/2023 | Suzuki | A61B 1/00144 600/133 | |
| 2023/0256193 | A1 * | 8/2023 | Nomura | A61M 5/007 206/364 | |

FOREIGN PATENT DOCUMENTS

| | | | |
|---|---|---|---|
| JP | 2003-235784 | A | 8/2003 |
| JP | 2008-126007 | A | 6/2008 |
| JP | 2013-220194 | A | 10/2013 |

* cited by examiner

ENDOSCOPE PACKAGE SYSTEM, MANUFACTURING METHOD OF ENDOSCOPE, AND HOLDING BODY

RELATED APPLICATION DATA

This application is based on and claims priority under 35 U.S.C. § 119 to U.S. Provisional Application No. U.S. 63/536,740, filed on Sep. 6, 2023, the entire contents of which are incorporated herein by reference.

BACKGROUND OF THE DISCLOSURE

1. Field of the Disclosure

The present disclosure relates to an endoscope including a bending portion, a manufacturing method of the endoscope, and a holding member of an endoscope body, where the bending portion is provided in part of an insertion portion having flexibility and configured to be actively bendable via pulling operations of bending wires.

2. Description of Related Art

Conventionally, endoscopes have been widely used, for example, in the medical field and the industrial field. Medical endoscopes used in the medical field include an insertion portion provided with flexibility, formed in an elongated tubular shape, and equipped with an image pickup unit and the like in a distal end portion; and an operation portion installed consecutively on a proximal end side of the insertion portion and equipped with various types of operation members and the like on an outer surface.

Regarding this form of conventional endoscope, endoscopes, the insertion portion of which is, for example, around 2 meters in total length have generally been put to practical use. Generally, such conventional endoscopes are stored in a container or the like of a predetermined form in a predetermined manner after manufacture, and then undergo a predetermined sterilization process (e.g., ethylene oxide gas (EOG) sterilization process or high-pressure steam sterilization process).

Regarding techniques for performing a sterilization process with an endoscope being stored in a container or the like, various proposals are made in Japanese Patent Application Laid-Open Publication Nos. 2002-533191, 2002-45335, 2003-235784, and the like.

Endoscopes disclosed in Japanese Patent Application Laid-Open Publication Nos. 2002-533191 and 2003-235784 include an elongate-shaped bag-like package, sheath, or tray that allows the insertion portion to be stored in stretched form.

An endoscope disclosed in Japanese Patent Application Laid-Open Publication No. 2002-45335 include a tray or case that allows the insertion portion to be stored by being looped in one predetermined direction.

SUMMARY OF THE DISCLOSURE

According to one aspect of the present disclosure, there is provided an endoscope package system including an endoscope, the endoscope including: a flexible insertion portion, in a length direction of the flexible insertion portion, the flexible insertion portion has a shape that includes a first winding direction and a second winding direction, the first winding direction is different from the second winding direction.

According to another aspect of the present disclosure, there is provided a manufacturing method of an endoscope, the method including: placing an insertion portion of an endoscope in a holding body such that the insertion portion has a shape that includes a first winding direction and a second winding direction; and sterilizing the endoscope and the holding body, the first winding direction is different from the second winding direction.

According to another aspect of the present disclosure, there is provided a holding body for use with an endoscope, the holding body includes a cavity configured to hold a flexible insertion portion of an endoscope in a shape that includes a first winding direction and a second winding direction, the holding body is selected from a group consisting of: a sheath of the endoscope, where the cavity is a lumen of the sheath, a tray, where the cavity is a channel in the tray, a clip, where the cavity is a groove in the clip, and a package, where the cavity is a track formed by two interior surfaces of the package adhered to each other.

DETAILED DESCRIPTION OF PREFERRED EMBODIMENTS

Figure 1:
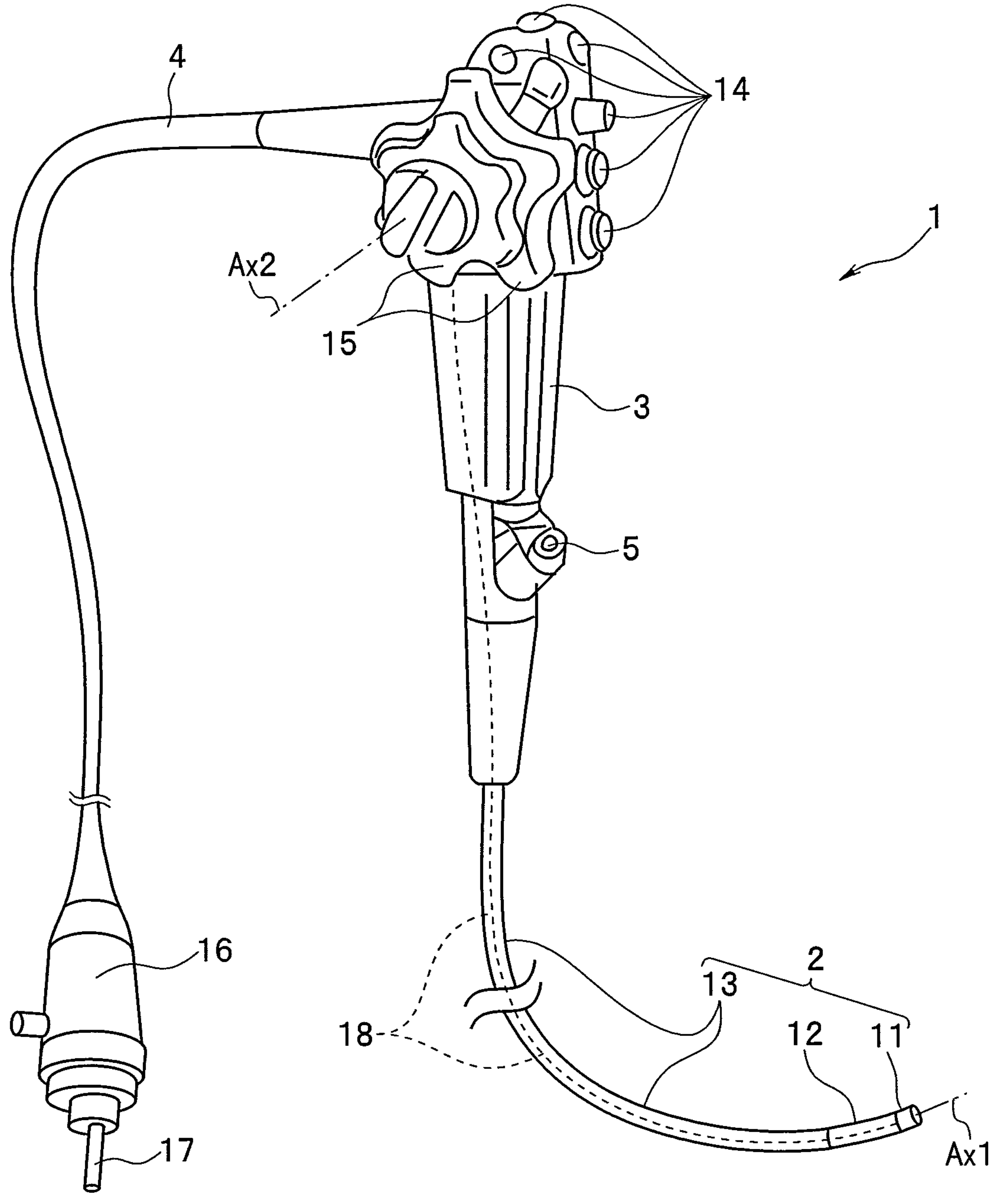
FIG. 1 is an external perspective view outlining an endoscope body included in an endoscope according to each embodiment of the present disclosure.

Generally, when a sterilization process is performed with respect to an endoscope stored in a container or the like with an insertion portion looped in a predetermined direction, bending wires (formed mainly of metal wire rod) tend to slacken while the insertion portion (formed mainly of resin or the like) shrinks under influence of heating and the like resulting from the sterilization process.

This may result in changes in amounts of hauling of the bending wires corresponding to amounts of operation of a bending operation knob. Amounts of shrinkage of the insertion portion differ between inside and outside a loop shape, which is a storage form. This might result in imbalance among the amounts of operation of multiple bending wires. This causes a problem that operability of the endoscope in terms of bending operation will become unstable.

Thus, various embodiments of the present disclosure can provide an endoscope that can reduce imbalance in the shrinkage of the insertion portion and prevent imbalance in slackening of bending wires even if a sterilization process involving heating is performed with respect to the endoscope stored in a container or the like and can thereby maintain stable operability while realizing compact storage of the endoscope in the container or the like as well as provide a manufacturing method of the endoscope and a holding member of an endoscope body.

The present disclosure will be described with reference to illustrated embodiments. Each of the drawings used in the following description are shown schematically, and to show each component in sizes that will allow the component to be recognized in the drawings, dimensional relationships, scale, and the like of different members may be varied from component to component. Therefore, the present disclosure is not limited to the illustrated forms regarding quantities, shapes, size ratios, and relative positional relationships of the individual components shown in each drawing.

Before describing individual embodiments of the endoscope package system according to the present disclosure, a schematic configuration of an endoscope body included in the endoscope will be described using FIGS. 1 and 2.

FIG. 1 is an external perspective view outlining an endoscope body included in an endoscope according to each embodiment of the present disclosure. FIG. 2 is a conceptual diagram showing, in a simplified manner, a bending mechanism of a bending portion incorporated in the endoscope body of FIG. 1.

As shown in FIG. 1, the endoscope body 1 includes an insertion portion 2, an operation portion 3, and a universal cable 4.

The insertion portion 2 is a component member inserted into a body cavity of a subject such as a living body. Starting from a distal end side, the insertion portion 2 is formed of a distal end portion 11, a bending portion 12, and a flexible tubular portion 13, which are connected consecutively. The insertion portion 2 is formed in a substantially elongated tubular shape (e.g., about 2 meters long). On a proximal end side, the insertion portion 2 is connected with the operation portion 3.

Although details are omitted, the endoscope body 1 is configured to allow insertion of an endoscopic treatment instrument (not illustrated). Specifically, the insertion portion 2 is provided with a treatment instrument passage conduit, which is a conduit for use to insert a non-illustrated treatment instrument and is extended from a distal end to a proximal end (not illustrated).

Various types of component members (not illustrated) including an image pickup unit and an illumination unit are provided inside the distal end portion 11. The image pickup unit is an electronic device unit made up of a photoelectric conversion element, an optical lens, and the like configured to acquire image information (still images and movies) about an object to be observed (e.g., body cavity inner walls of an organ) in the subject. The illumination unit is a component unit including an optical element configured to illuminate a region to be observed including a lesion site in the subject by emitting a light flux forward from a distal end surface of the distal end portion 11, where the light flux is led from an after-mentioned light source device (not illustrated).

The operation portion 3 is connected to a proximal end of the insertion portion 2. The operation portion 3 includes a plurality of operation members 14, a bending operation knob 15, and a treatment instrument insertion port 5.

The operation portion 3 is substantially box-shaped as a whole, making up a grasping portion to be grasped by a surgeon or the like, who is a user of the endoscope body 1. As described above, the insertion portion 2 is connected to the operation portion 3, extending in one direction.

The plurality of operation members 14 and the bending operation knob 15 are operation members for use to perform various types of operations of the endoscope body 1. In particular, the bending operation knob 15 is used to manipulate or lock/unlock a bending state or bending direction of the bending portion 12.

Thus, the bending operation knob 15 is provided as an operation member capable of causing the bending portion 12, by acting on bending wires 18 and a drive mechanism 19 described later (see FIG. 2), to actively bend around a major axis Ax1 of the insertion portion 2.

The bending wires 18 are inserted in the insertion portion 2 and the operation portion 3, running from a distal end of the bending portion 12 to the bending operation knob 15. Note that outlines of a configuration and working of a bending mechanism will be described later (see FIG. 2).

The plurality of operation members 14 and the bending operation knob 15 are provided, respectively, in predetermined positions on an outer surface of the operation portion 3. In this case, the bending operation knob 15 is provided rotatably around a rotation axis denoted by reference sign Ax2 in FIG. 1.

The treatment instrument insertion port 5 is provided at a predetermined position close to a distal end of the operation portion 3. The treatment instrument insertion port 5 is a proximal end-side opening of the treatment instrument passage conduit (not illustrated) of the insertion portion 2. The treatment instrument passage conduit is connected on the distal end side to a distal end opening (not illustrated) of the distal end portion 11. With such a configuration, a distal end of a treatment instrument (not illustrated) inserted through the treatment instrument insertion port 5 is configured to be able to project outward through the distal end opening of the distal end portion 11.

The universal cable 4 is a composite cable extending from a side face of the operation portion 3. A scope connector 16 is disposed on a distal end of the universal cable 4. The scope connector 16 is a connector member connected to a video processor (not illustrated), which is an external device including a light source device. The scope connector 16 includes a light guide connector 17 as well as electrical contacts.

A light guide bundle (not illustrated), various types of signal lines (not illustrated), and the like are passed through the scope connector 16, the universal cable 4, the operation portion 3, and the distal end portion 11 of the insertion portion 2. Here, the light guide bundle is a component member configured to transmit a light flux emitted from a light source device included in a non-illustrated video processor to the distal end portion 11 of the insertion portion 2. The light flux transmitted to the distal end portion 11 by the light guide bundle is emitted, as illuminating light for use to illuminate an object to be observed, from the illumination unit (not illustrated) provided in the distal end portion 11.

The various types of signal lines include an image pickup cable used to transmit an image signal acquired by an image pickup unit (not illustrated) provided in the distal end portion 11 to a video processor (not illustrated) and a control signal cable used to transmit a control signal issued from the video processor to component units such as the image pickup unit.

Next, a bending mechanism used for bending operation of the bending portion 12 will be described below briefly using FIG. 2. The bending mechanism used for bending operation of the bending portion 12 is disposed inside the endoscope body 1 as shown in FIG. 2.

The bending mechanism includes the bending operation knob 15, the bending wires 18, and the drive mechanism 19. In this case, the bending portion 12 has a typical structure formed by coupling, for example, a plurality of annular members. Thus, regarding the bending portion 12 itself, illustration and description of a detailed configuration will be omitted. It is assumed that the bending portion 12 is configured to be bendable around the major axis Ax1 of the insertion portion 2.

The bending operation knob 15, which is a bending operation member, is an operation member provided rotatably around the rotation axis Ax2 (in the direction along arrow R in FIG. 2) with respect to the operation portion 3 of the endoscope body 1. The bending operation knob 15 is connected with the bending portion 12 of the insertion portion 2 of the endoscope body 1 via the drive mechanism 19 and the bending wires 18.

The bending wires 18 are connected at the proximal end to the bending operation knob 15 via the drive mechanism 19 and connected at the distal end to a distal end area of the bending portion 12 of the insertion portion 2. In this case, the bending wires 18 are passed through the operation portion 3 from the insertion portion 2. The bending wires 18 are placed advanceably/retractably in directions along the major axis Ax1 of the insertion portion 2 (in directions along arrows X1 and X2 in FIG. 2) in response to rotating operation of the bending operation knob 15.

A plurality of bending wires 18 are provided. Specifically, for example, in the configuration example shown in FIG. 2, the endoscope body 1 includes two bending wires **18*a* and 18*b*. When two bending wires 18** are provided in this way, bending operation can be performed in one of, for example, up-and-down direction and left-and-right direction.

Note that it is adequate if at least two bending wires 18 are provided, and thus apart from the above configuration example, for example, four bending wires may be provided. In that case, the four bending wires 18 allow bending operations to be performed in four directions: up-and-down and left-and-right directions. Therefore, two operation knobs are provided: a left-and-right operation knob and an up-and-down operation knob.

The drive mechanism 19 of the bending mechanism is a mechanical device that accepts a rotating operation of the bending operation knob 15 as input and transforms the rotating operation into an amount of force used to pull or relax the bending wires 18. The drive mechanism 19 of a typical form applied to conventional endoscopes is used. Thus, regarding the drive mechanism 19 itself, again illustration and description of a detailed configuration will be omitted.

Working of the bending mechanism configured as described above is roughly as follows. First, it is assumed that the bending operation knob 15 is rotated in a predetermined direction along arrow R (e.g., in the direction along arrow R1 in FIG. 2). Then, rotating operation input of the bending operation knob 15 is transmitted to the bending wires 18 via the drive mechanism 19.

Figure 2:
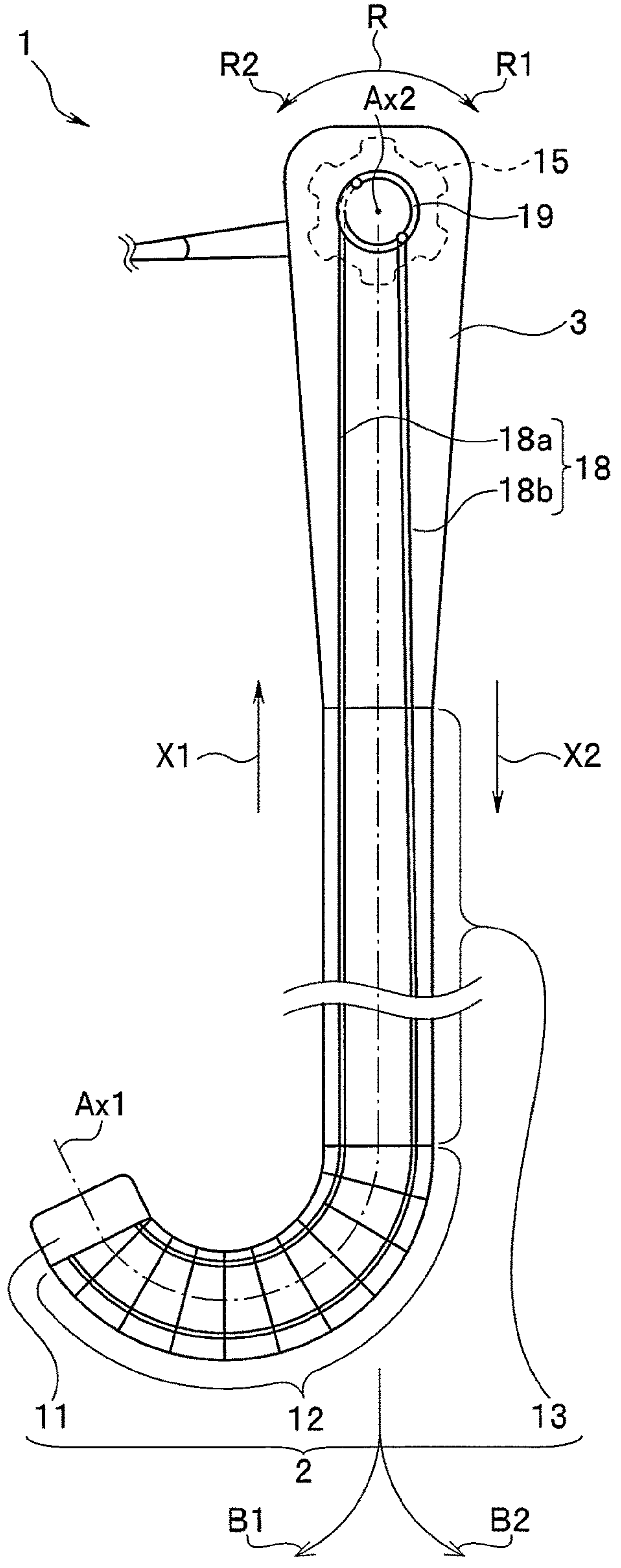
FIG. 2 is a conceptual diagram showing, in a simplified manner, a bending mechanism of a bending portion incorporated in the endoscope body of FIG. 1.

In so doing, one **18*a* of the two bending wires 18 is pulled in the direction of arrow X1 in FIG. 2. At the same time, the other 18*b* of the two bending wires 18 is relaxed in the direction of arrow X2 in FIG. 2. Consequently, the bending portion 12 of the insertion portion 2 bends in the direction of reference sign B1**.

Now, if the bending operation knob 15 is rotated in an opposite direction (the direction along arrow R2), the wire **18*a* moves in a relaxing direction and the wire 18*b* moves in a pulling direction. Consequently, the bending portion 12 bends in the direction of reference sign B2**.

Thus, the schematic configuration of the endoscope body 1 and the working of the bending mechanism have been described above. Note that as the endoscope body 1 to which the present disclosure is applied, for example, an endoscope of a single-use form is assumed. However, the present disclosure is not limited to single-use endoscopes, and is equally applicable, for example, to so-called reusable endoscopes that can be reused after cleaning.

An endoscope according to each embodiment of the present disclosure will be described in detail below.

Figure 3:
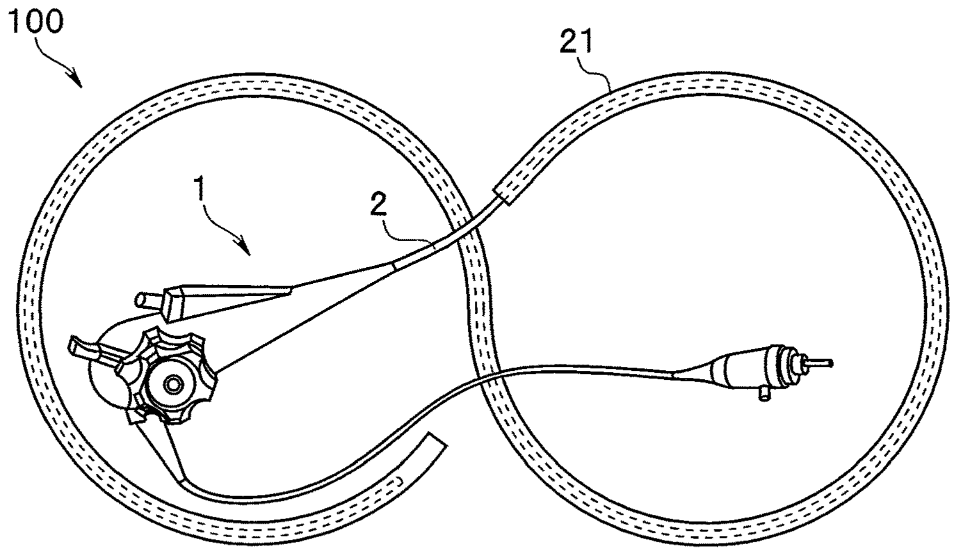
FIG. 3 is a conceptual diagram showing an endoscope according to a first embodiment of the present disclosure, where an insertion portion of an endoscope body is stored in a first holding sheath.
Figure 4:
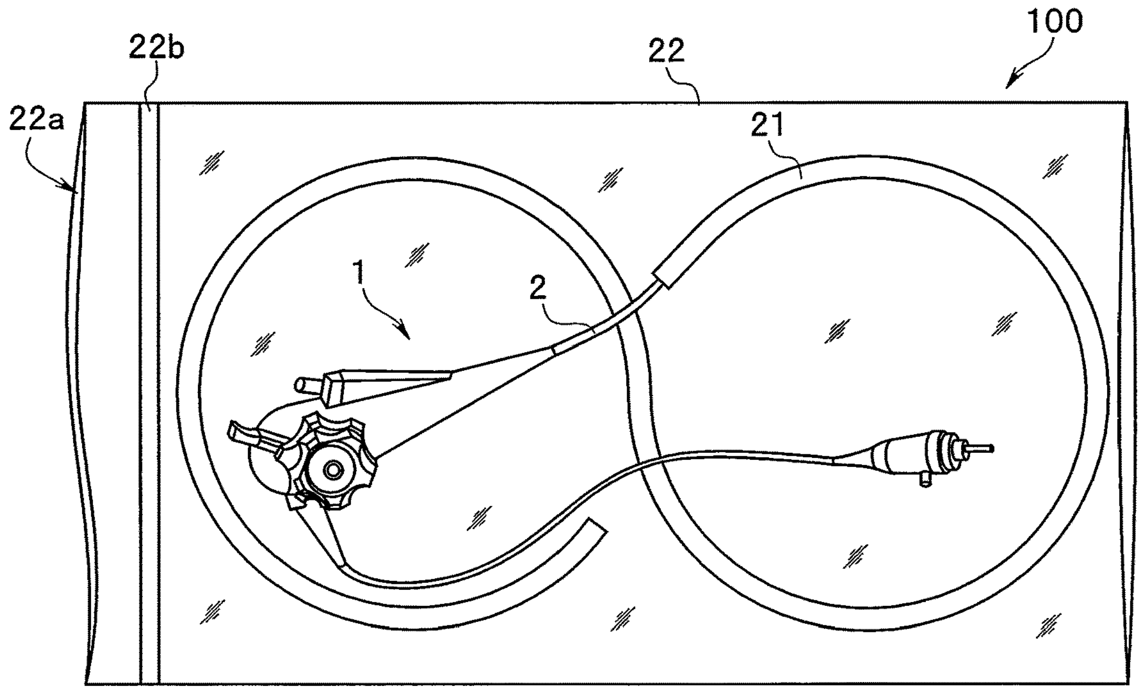
FIG. 4 is a conceptual diagram showing how the endoscope of FIG. 3 is stored in a sterilizing package.

First, an endoscope according to a first embodiment of the present disclosure will be described below using FIGS. 3 and 4. FIGS. 3 and 4 are diagrams showing the endoscope according to the first embodiment of the present disclosure, of which FIG. 3 is a conceptual diagram showing the endoscope according to the first embodiment of the present disclosure, where an insertion portion of an endoscope body is stored in a first holding sheath; and FIG. 4 is a conceptual diagram showing how the endoscope of FIG. 3 is stored in a sterilizing package.

As shown in FIG. 3, the endoscope 100 according to the present embodiment includes the endoscope body 1 and a first holding sheath 21.

The endoscope body 1 includes a flexible insertion portion 2. Note that the configuration of the endoscope body 1 is as described above (see FIGS. 1 and 2).

The first holding sheath 21 is a holding member (holding body) for use to hold the insertion portion 2 in a predetermined shape. The first holding sheath 21 is a member placed on an outer side of the insertion portion 2. The first holding sheath 21 is a flexible sheath with an elongated tubular shape. The first holding sheath 21 is a container having a cavity that covers an outer surface of the insertion portion 2 and is capable of storing substantially an entire region from a distal end of the insertion portion 2 to near the proximal end.

The holding member of the endoscope according to the present disclosure is formed to have at least two different winding directions. Part of the holding member is substantially S-shaped. In a length direction of the insertion portion 2, the insertion portion 2 has a shape that includes a first winding direction and a second winding direction. The first winding direction is different from the second winding direction. In other word, the first winding direction is a clockwise direction, and the second winding direction is a counterclockwise direction.

The first holding sheath 21, which is a holding member illustrated by example in the present embodiment, is substantially S-shaped as a whole as shown in FIGS. 3 and 4. In this case, while having flexibility, the first holding sheath 21 is formed to have some hardness such that the predetermined shape (substantially an S-like shape) will be maintained. The first holding sheath 21 is formed, for example, of high-impact polystyrene (HIPS), polyvinyl chloride (PVC), glycol modified polyethylene terephthalate (G-PET or PETG), or the like.

As shown in FIG. 4, the endoscope 100 according to the present embodiment further includes a sterilizing package 22.

The sterilizing package 22 is a packaging material capable of housing the endoscope body 1 and the first holding sheath 21 (a holding member). The sterilizing package 22 is formed of a material pervious to sterilizing gas.

As shown in FIG. 4, the sterilizing package 22 illustrated by example in the present embodiment has a bag-like form with an opening portion 22*a*. The sterilizing package 22 with the bag-like form has a fastener 22*b* near the opening portion 22*a* to seal up the opening portion 22*a*.

As shown in FIG. 4, the sterilizing package 22 has a size that allows the endoscope body 1 to be stored in the sterilizing package 22 with the insertion portion 2 stored in the first holding sheath 21. In this case, the sterilizing package 22 can store the first holding sheath 21 with the predetermined shape (substantially an S-like shape) being maintained.

In the case of the endoscope 100 according to the present embodiment configured as described above, before a sterilization process is performed, the insertion portion 2 of the endoscope body 1 is in a state of being stored in the first holding sheath 21 (the state shown in FIG. 3). In this state (the state shown in FIG. 3), the endoscope body 1 and the first holding sheath 21 are stored in the sterilizing package 22.

The sterilizing package 22 has the opening portion 22*a* closed by the fastener 22*b*. Consequently, the sterilizing package 22 is sealed internally. This state is shown in FIG. 4. In the state shown in FIG. 4, a predetermined sterilization process (e.g., ethylene oxide gas sterilization process) is performed with respect to the endoscope 100.

As described above, according to the first embodiment, before a sterilization process is performed with respect to the endoscope 100, the insertion portion 2 of the endoscope body 1 is stored in the first holding sheath 21 (a holding member). The first holding sheath 21 is formed to have at least two different winding directions and part of the first holding sheath 21 is substantially S-shaped. The endoscope body 1 and the first holding sheath 21 arranged in this way are stored in the sterilizing package 22 in a sealed state. The sterilization process is performed in this state.

Consequently, even if the endoscope 100 is undergoing a sterilization process, the predetermined shape of the insertion portion 2 is maintained by the first holding sheath 21 (a holding member). In this case, the predetermined shape is a shape having two different winding directions rather than a shape looped in a predetermined direction. The shape includes a first loop formed by the insertion portion 2 extending in the first winding direction, and a second loop formed by the insertion portion 2 extending in the second winding direction. The insertion portion 2 includes a first side surface and a second side surface, the first side surface opposes the second side surface relative to a longitudinal axis of the insertion portion 2. In the first loop, the first side surface is on an inner diameter surface of the first loop and the second side surface is on an outer diameter surface of the first loop. In the second loop, the second side surface is on an inner diameter surface of the second loop and the first side surface is on an outer diameter surface of the second loop. A sum of a length of the inner diameter surface of the first loop and a length of the outer diameter surface of the second loop defines a first total length. A sum of a length of the outer diameter surface of the first loop and a length of the inner diameter surface of the second loop defines a second total length. The first total length equals the second total length.

According to the present embodiment, specifically, the predetermined shape of the first holding sheath 21 is substantially an S-like shape. This shape allows the insertion portion 2 to be stored in a compact state when the endoscope body 1 and the first holding sheath 21 are stored in the sterilizing package 22.

With this configuration, even if heated in the sterilization process, the insertion portion 2 is free from being shrunk only in a specific direction. Besides, the bending wires 18 inserted into the insertion portion 2 are free from slackening excessively in a specific direction. A first wire of the bending wires 18 extends from a proximal end of the insertion portion 2 to a distal end of the insertion portion 2 within the first side surface of the insertion portion 2. A second wire of the bending wires 18 extends from the proximal end of the insertion portion 2 to the distal end of the insertion portion 2 within the second side surface of the insertion portion 2. With the insertion portion 2 is arranged in the shape, a length of the first wire equals a length of the second wire. With the insertion portion 2 is arranged in the shape, the first wire has a first length, and the second wire has a second length, and the first length equals the second length. With the insertion portion 2 is arranged in a straight line, the first wire has a third length, and the second wire has a fourth length, and the third length equals the fourth length. The first length does not equal the third length, and the second length does not equal the fourth length.

Therefore, even if a sterilization process involving heating is performed with respect to the insertion portion 2, imbalance in the shrinkage of the insertion portion 2 can be reduced. At the same time, imbalance in slackening of bending wires does not occur. Therefore, even if a sterilization process involving heating is performed, bending operability of the endoscope body 1 is not impaired and stable operability can be maintained.

Figure 5:
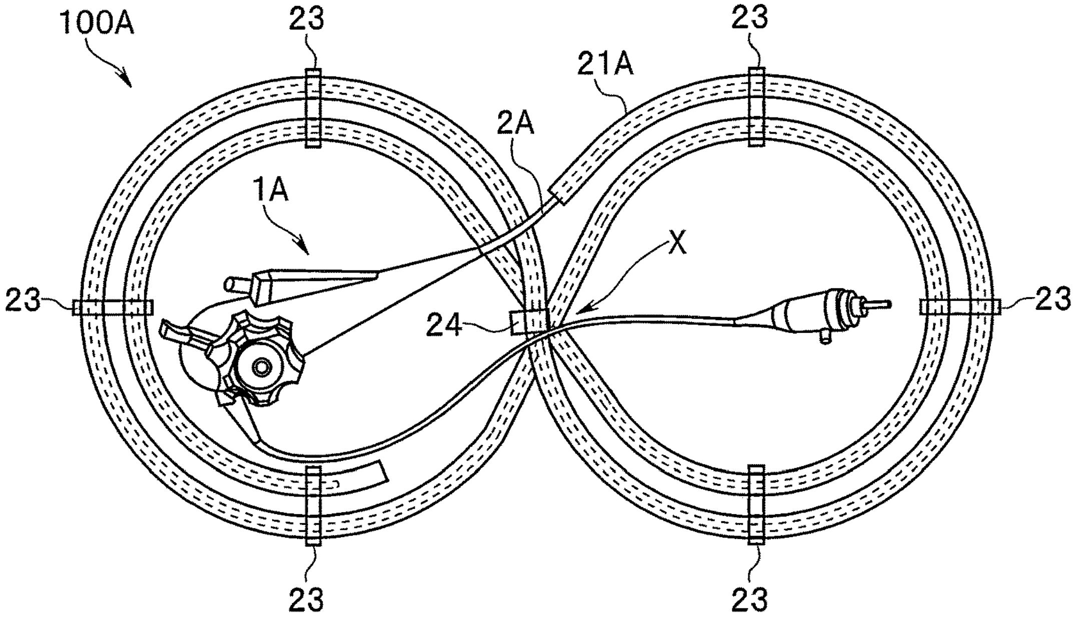
FIG. 5 is a conceptual diagram showing an endoscope according to a second embodiment of the present disclosure, where an insertion portion of an endoscope body is stored in a second holding sheath.
Figure 6:
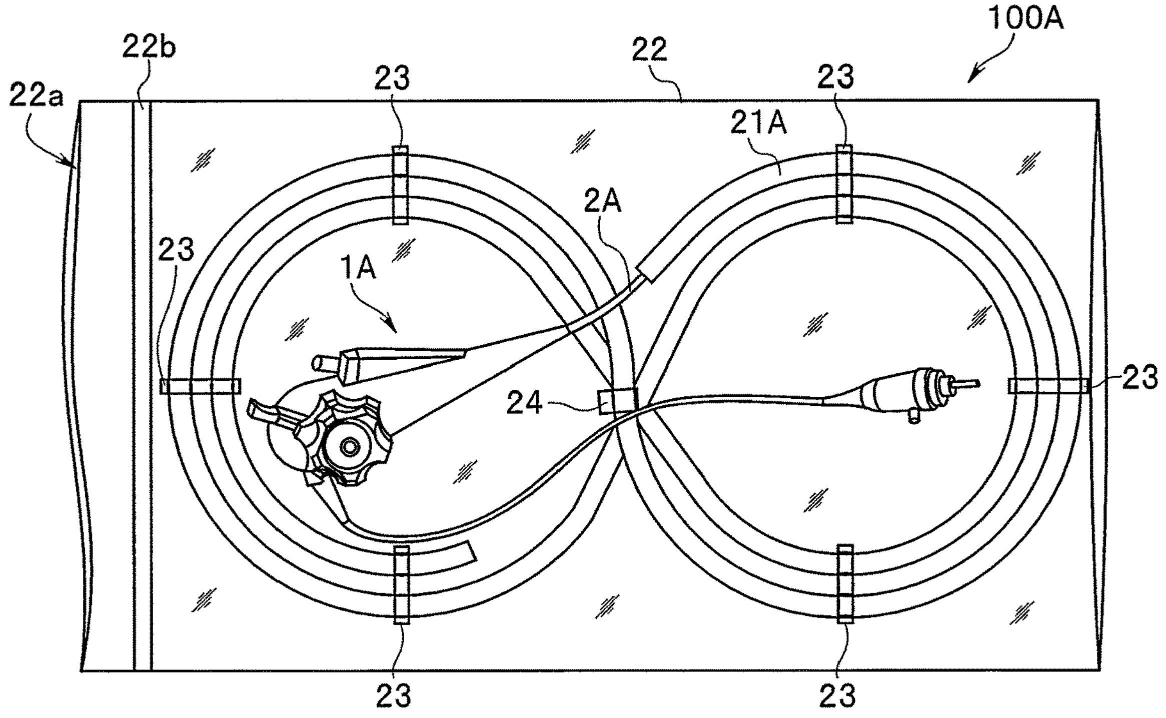
FIG. 6 is a conceptual diagram showing how the endoscope of FIG. 5 is stored in a sterilizing package.
Figure 7:
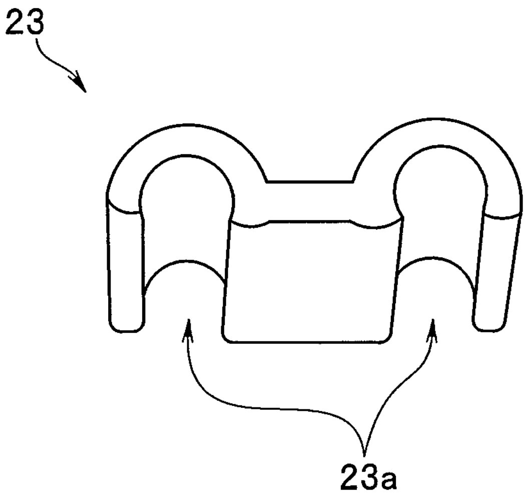
FIG. 7 is an external perspective view of a first fixing part picked out solely from the endoscope of FIG. 5 and shown in an enlarged form.
Figure 8:
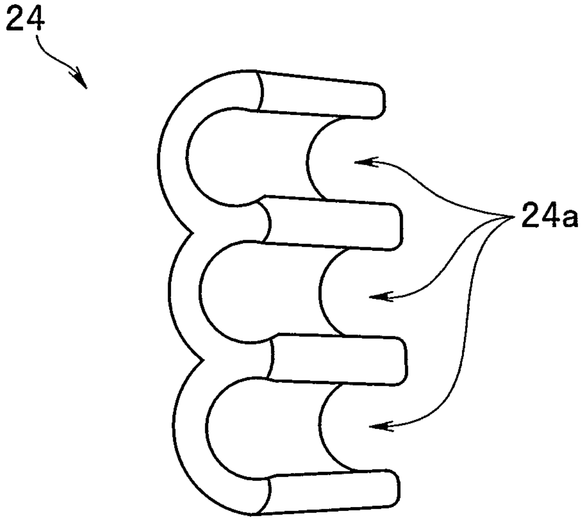
FIG. 8 is an external perspective view of a second fixing part picked out solely from the endoscope of FIG. 5 and shown in an enlarged form.

Next, an endoscope according to a second embodiment of the present disclosure will be described below using FIGS. 5 to 8. FIGS. 5 to 8 are diagrams showing the endoscope according to the second embodiment of the present disclosure; of which FIG. 5 is a conceptual diagram showing the endoscope according to the second embodiment of the present disclosure, where an insertion portion of an endoscope body is stored in a second holding sheath; FIG. 6 is a conceptual diagram showing how the endoscope of FIG. 5 is stored in a sterilizing package; FIG. 7 is an external perspective view of a first fixing part picked out solely from the endoscope of FIG. 5 and shown in an enlarged form; and FIG. 8 is an external perspective view of a second fixing part picked out solely from the endoscope of FIG. 5 and shown in an enlarged form.

Basic configuration of the present embodiment is substantially the same as the first embodiment described above. The present embodiment has a configuration corresponding to an endoscope body 1A equipped with an insertion portion 2A longer than the insertion portion 2 of the endoscope body 1 applied in the first embodiment.

A holding member according to the present embodiment differs from the configuration of the first embodiment described above in that a second holding sheath 21A is used. Thus, in the present embodiment, description of the same members as the first embodiment is omitted, and only different part will be described in detail below.

An endoscope 100A according to the present embodiment includes the endoscope body 1A and the second holding sheath 21A as shown in FIG. 5.

As described above, the endoscope body 1A includes the longer and flexible insertion portion 2A. A configuration of the endoscope body 1A itself is substantially the same as the first embodiment described above (see FIGS. 1 and 2).

The second holding sheath 21A is a holding member for use to hold the insertion portion 2A in a predetermined shape. Basic configuration of the second holding sheath 21A is substantially the same as the first holding sheath 21 according to the first embodiment described above.

The second holding sheath 21A is the same as the first holding sheath 21 according to the first embodiment described above in that the second holding sheath 21A is formed to have at least two different winding directions and formed as a holding member, part of which is substantially S-shaped.

The second holding sheath 21A, which is a holding member illustrated by example in the present embodiment, differs in being substantially 8-shaped as a whole as shown in FIGS. 5 and 6. In this case, while having flexibility, the second holding sheath 21A is formed to have some hardness such that the predetermined shape (substantially an 8-like shape) will be maintained.

The second holding sheath 21A illustrated by example in the present embodiment forms a plurality of substantially 8-like shapes in a same plane. Consequently, as shown in FIG. 5 and the like, the second holding sheath 21A forms a plurality of substantially 8-like shapes when viewed from above. In this case, a plurality of first fixing parts 23 (clip) is a holding member for use to hold the endoscope body 1. The plurality of first fixing parts 23 are provided to hold the substantially 8-like shape on the outer circumferential side and the substantially 8-like shape on the inner circumferential side in position on one plane.

As shown in FIG. 7, each of the first fixing parts 23 has a plurality of grooved portions 23*a* formed to allow the second holding sheath 21A to be inserted. By fixing part of the second holding sheath 21A to each of the plurality of grooved portions 23*a*, the part of the second holding sheath 21A can be fixed in parallel. The plurality of grooved portions 23*a* are configured to receive the insertion portion 2.

As shown in FIG. 5, in a region (indicated by reference sign X in FIG. 5) where the plurality of substantially 8-like shapes intersect, the second holding sheath 21A is placed by overlapping in a vertical direction on the plane. Thus, in the intersection region X, a second fixing part 24 is provided to hold part of the second holding sheath 21A overlapping vertically.

As shown in FIG. 8, the second fixing part 24 has a plurality of grooved portions 24*a* formed to allow the second holding sheath 21A to be inserted in a manner substantially the same as the first fixing parts 23. By fixing part of the second holding sheath 21A to each of the plurality of grooved portions 24*a*, the part of the second holding sheath 21A can be fixed in parallel in the vertical direction. Note that the first fixing parts 23 and the second fixing part 24 are not indispensable. This is because the second holding sheath 21A itself is formed to have such hardness that a predetermined shape can be maintained.

The endoscope 100A according to the present embodiment further includes the sterilizing package 22 as shown in FIG. 6. The sterilizing package 22 is a packaging material capable of housing the endoscope body 1A and the second holding sheath 21A (a holding member), and is a package of the same bag-like form as the package shown in the first embodiment.

As shown in FIG. 6, the sterilizing package 22 has a size that allows the endoscope body 1A (the endoscope 100A) to be stored in the sterilizing package 22 with the insertion portion 2A stored in the second holding sheath 21A. The sterilizing package 22 can store the second holding sheath 21A with the predetermined shape (substantially an 8-like shape) being maintained.

Working of the endoscope 100A according to the second embodiment configured as described above is substantially the same as the first embodiment described above. The second embodiment can accommodate even the endoscope body 1A equipped with the long insertion portion 2A and achieve effects exactly the same as the first embodiment.

Whereas a configuration example in which the second holding sheath 21A is folded into a plurality of substantially 8-like shapes on the same plane has been shown in the present embodiment, the present disclosure is not limited to this form. Other conceivable forms include a form in which a plurality of substantially 8-like shapes are placed stacking in a vertical direction on one plane.

Figure 9:
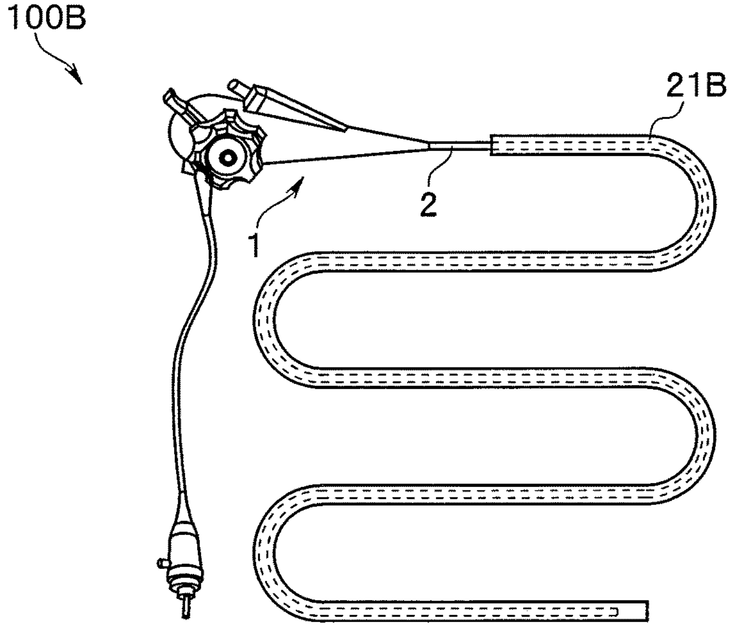
FIG. 9 is a conceptual diagram showing an endoscope according to a third embodiment of the present disclosure, where an insertion portion of an endoscope body is stored in a third holding sheath.
Figure 10:
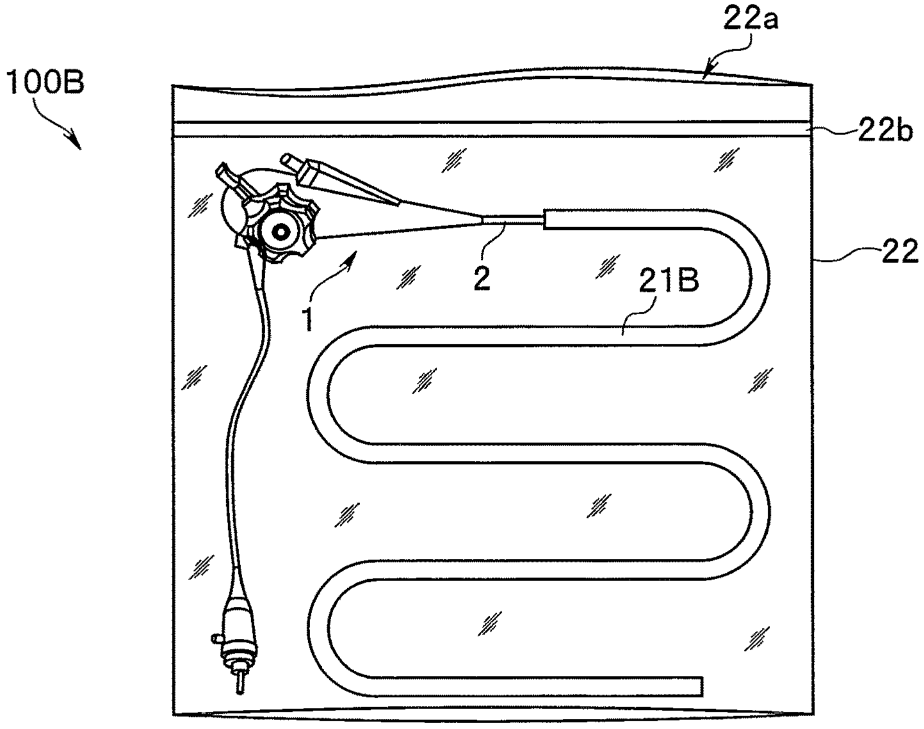
FIG. 10 is a conceptual diagram showing how the endoscope of FIG. 9 is stored in a sterilizing package.

Next, an endoscope according to a third embodiment of the present disclosure will be described below using FIGS. 9 and 10. FIGS. 9 and 10 are diagrams showing the endoscope according to the third embodiment of the present disclosure. FIG. 9 is a conceptual diagram showing the endoscope according to the third embodiment of the present disclosure, where an insertion portion of an endoscope body is stored in a third holding sheath. FIG. 10 is a conceptual diagram showing how the endoscope of FIG. 9 is stored in a sterilizing package.

Basic configuration of the present embodiment is substantially the same as the first embodiment described above. In the present embodiment, a configuration of a holding member (a third holding sheath 21B) differs from the configuration of the first embodiment (the first holding sheath 21). Thus, in the present embodiment, description of the same members as the first embodiment is omitted, and only different part will be described in detail below.

An endoscope 100B according to the present embodiment includes the endoscope body 1 and the third holding sheath 21B as shown in FIG. 9.

The endoscope body 1 is the same as the endoscope body 1 applied in the first embodiment described above. The configuration of the endoscope body 1 itself is as described above (see FIGS. 1 and 2).

The third holding sheath 21B is a holding member for use to hold the insertion portion 2 in a predetermined shape. Basic configuration of the third holding sheath 21B is substantially the same as the first holding sheath 21 according to the first embodiment described above.

The third holding sheath 21B is the same as the first holding sheath 21 according to the first embodiment described above in that the third holding sheath 21B is formed to have at least two different winding directions and formed as a holding member, part of which is substantially S-shaped.

The third holding sheath 21B, which is a holding member illustrated by example in the present embodiment, differs in being substantially wave-shaped or meander-shaped as a whole as shown in FIGS. 9 and 10. In this case again, while having flexibility, the third holding sheath 21B is formed to have some hardness such that the predetermined shape (substantially a wave shape or a meander shape) will be maintained. The meander shape includes a plurality of straight portions and a curved portion, the curved portion connects a respective two straight portions of the plurality of straight portions. The plurality of straight portions are in parallel to each other. A first curved portion of the plurality of curved portions connects a distal end of a first straight portion of the plurality of straight portions, and a second curved portion of the plurality of curved portions connects a distal end of the second straight portion to a proximal end of a third straight portion of the plurality of straight portions. A third curved portion of the plurality of curved portions connects a distal end of the third straight portion to a proximal end of a fourth straight portion of the plurality of straight portions.

The endoscope 100B according to the present embodiment further includes the sterilizing package 22 as shown in FIG. 10. The sterilizing package 22 is a packaging material capable of housing the endoscope body 1 and the third holding sheath 21B (a holding member), and is a package of the same bag-like form as the package shown in the first embodiment.

As shown in FIG. 10, the sterilizing package 22 also has a size that allows the endoscope body 1 to be stored in the sterilizing package 22 with the insertion portion 2 stored in the third holding sheath 21B. The sterilizing package 22 can store the third holding sheath 21B with the predetermined shape (substantially a wave shape or a meander shape) being maintained.

Working of the endoscope 100B according to the third embodiment configured as described above is substantially the same as the first embodiment described above. The third embodiment can achieve effects exactly the same as the first embodiment.

Figure 11:
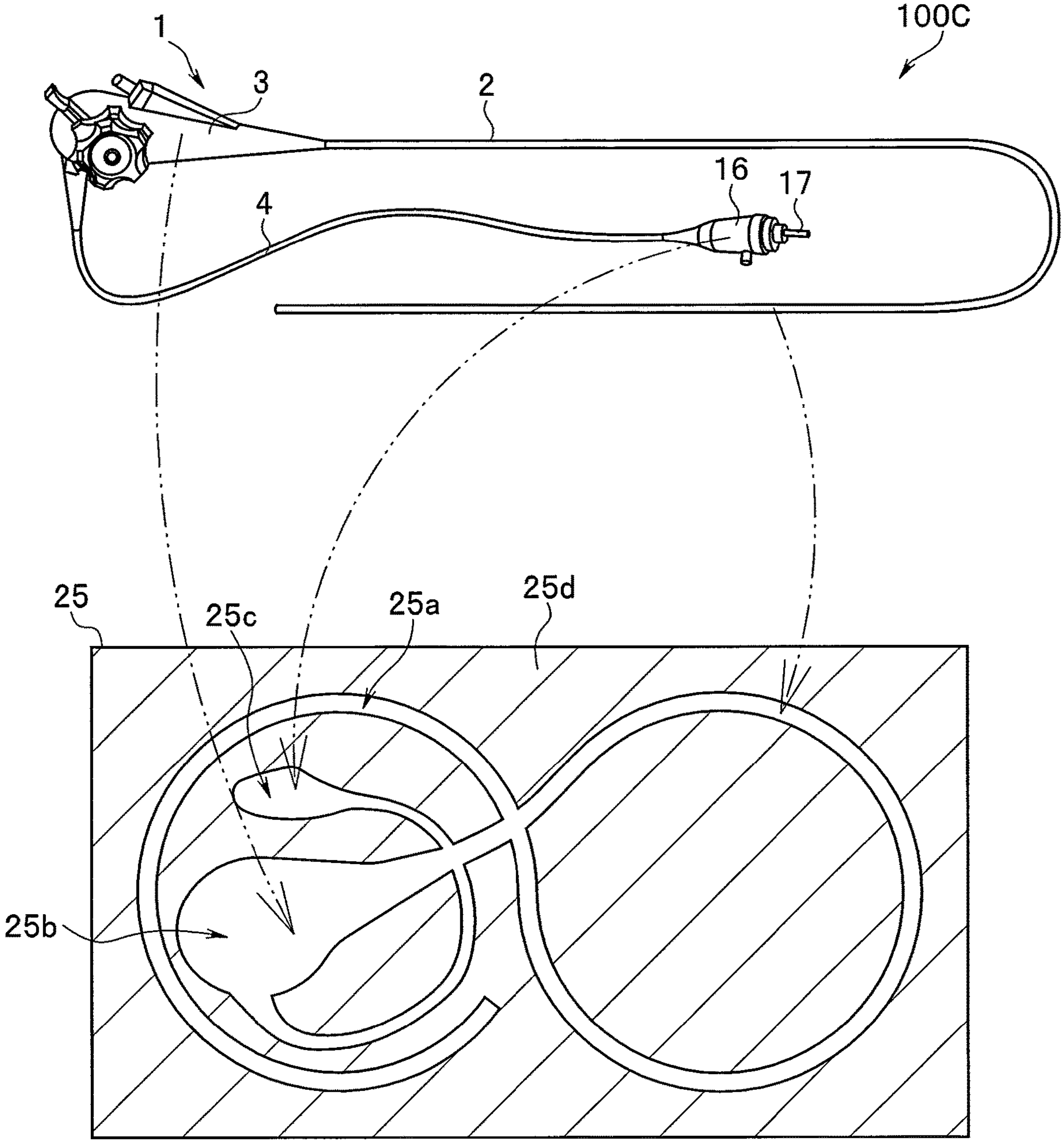
FIG. 11 is a conceptual diagram showing an endoscope body and a first holding tray included in an endoscope according to a fourth embodiment of the present disclosure.
Figure 12:
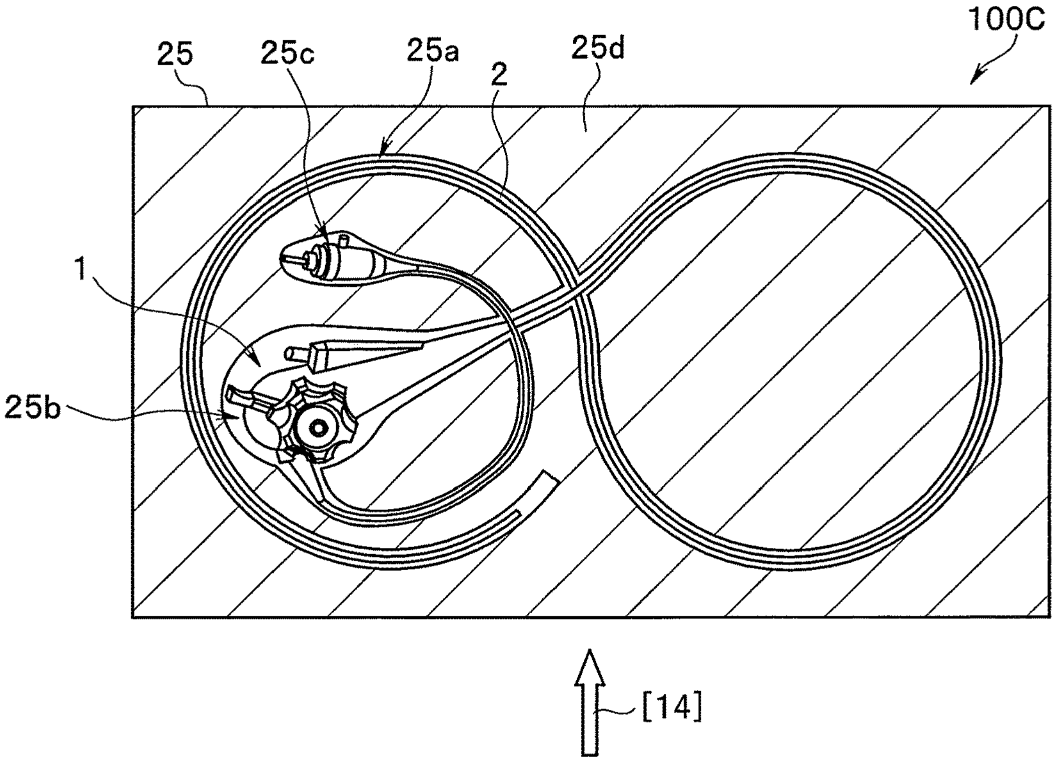
FIG. 12 is a conceptual diagram showing how the endoscope body of the endoscope of FIG. 11 is housed in the first holding tray.
Figure 13:
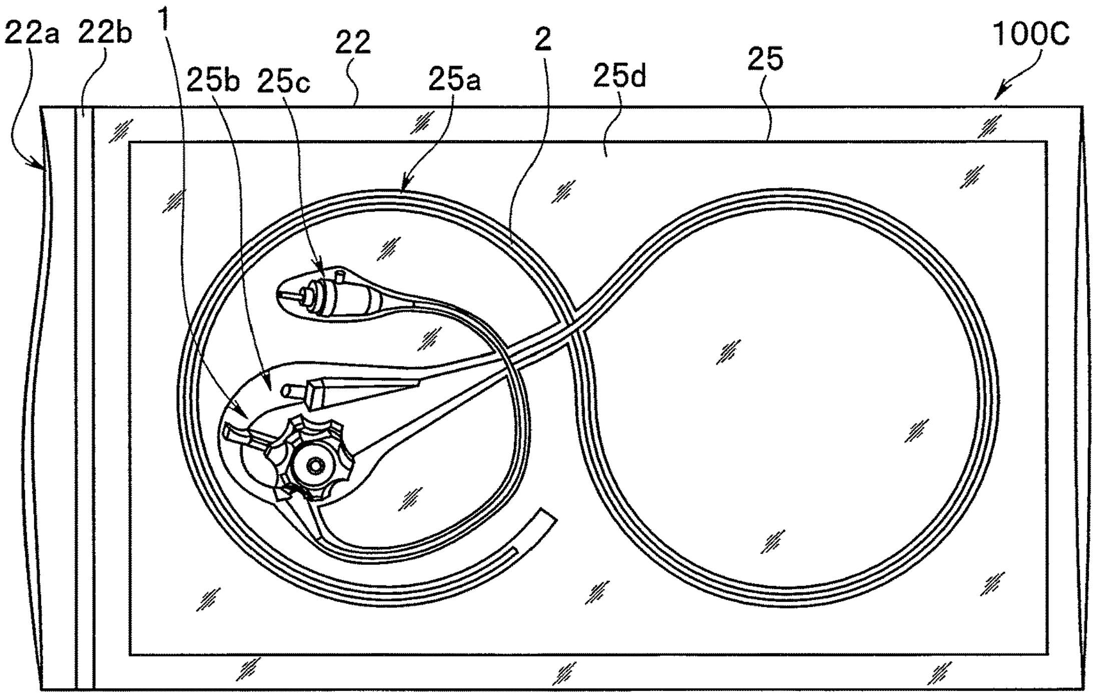
FIG. 13 is a conceptual diagram showing how the endoscope of FIG. 12 is stored in a sterilizing package.

Next, an endoscope according to a fourth embodiment of the present disclosure will be described below using FIGS. 11 to 13. FIGS. 11 to 13 are diagrams showing the endoscope according to the fourth embodiment of the present disclosure, of which FIG. 11 is a conceptual diagram showing an endoscope body and a first holding tray included in the endoscope according to the fourth embodiment of the present disclosure; FIG. 12 is a conceptual diagram showing how the endoscope body of the endoscope of FIG. 11 is housed in the first holding tray; and FIG. 13 is a conceptual diagram showing how the endoscope of FIG. 12 is stored in a sterilizing package.

Basic configuration of the present embodiment is substantially the same as the first embodiment described above. The present embodiment differs from the first embodiment in the form of a holding member. The holding member according to the present embodiment differs in that a first holding tray 25 is applied instead of the first holding sheath 21 according to the first embodiment. Thus, in the present embodiment, description of the same members as the first embodiment is omitted, and only different part will be described in detail below.

An endoscope 100C according to the present embodiment includes the endoscope body 1 and the first holding tray 25 as shown in FIGS. 11 and 12.

The endoscope body 1 is the same as the endoscope body 1 applied in the first embodiment described above. The configuration of the endoscope body 1 itself is as described above (see FIGS. 1 and 2).

The first holding tray 25 is a holding member for use to hold the endoscope body 1. In this case, the first holding tray 25 holds the insertion portion 2 in a predetermined shape. The first holding tray 25 is a container having a cavity capable of housing the endoscope body 1.

Therefore, the first holding tray 25 includes an insertion portion housing groove 25*a* (channel), an operation portion housing groove 25*b*, and a connector housing groove 25*c*. The multiple housing grooves (25*a*, 25*b*, and 25*c*) form a contiguous concave groove. Note that the first holding tray 25 is formed, for example, of high-impact polystyrene (HIPS), polyvinyl chloride (PVC), glycol modified polyethylene terephthalate (G-PET or PETG), or the like.

Note that the region indicated by oblique lines in FIGS. 11 and 12 represents a flat surface 25*d* of the first holding tray 25. In FIGS. 11 and 12, the non-hatching regions represent the multiple housing grooves (25*a*, 25*b*, and 25*c*) described above. In FIG. 13, the oblique lines on the flat surface 25*d* are omitted to avoid complicating the drawing.

The insertion portion housing groove 25*a* is formed in a concave groove shape that can house substantially an entire area of the insertion portion 2 from the distal end to near the proximal end by maintaining a predetermined shape. Of the first holding tray 25, which is a holding member illustrated by example in the present embodiment, the insertion portion housing groove 25*a* is substantially S-shaped as a whole as shown in FIGS. 11 and 12.

The operation portion housing groove 25*b* is formed in a concave groove shape that can house the operation portion 3. The insertion portion housing groove 25*b* is formed contiguously with the insertion portion housing groove 25*a*.

The connector housing groove 25*c* is formed in a concave groove shape that can house the scope connector 16, the light guide connector 17, and the universal cable 4. The connector housing groove 25*c* is formed contiguously with the insertion portion housing groove 25*b*.

In this way, the insertion portion housing groove 25*a* of the first holding tray 25 is the same as the holding members of other embodiments described above in being formed to have at least two different winding directions and formed as a holding member, part of which is substantially S-shaped.

The endoscope 100C according to the present embodiment further includes the sterilizing package 22 as shown in FIG. 13. The sterilizing package 22 is a packaging material capable of housing the endoscope body 1 and the first holding tray 25 (a holding member), and is a package of the same bag-like form as the package shown in the first embodiment described above.

As shown in FIG. 13, the sterilizing package 22 also has a size that allows the first holding tray 25 to be stored with the endoscope body 1 being stored in the first holding tray 25. Thus, the sterilizing package 22 can store the first holding tray 25 with the predetermined shape (substantially an S-like shape) of the insertion portion 2 being maintained.

In the case of the endoscope 100C according to the present embodiment configured as described above, before a sterilization process is performed, the endoscope body 1 is in a state of being stored in the multiple housing grooves (25*a*, 25*b*, and 25*c*) of the first holding tray 25 (the state shown in FIG. 12). In this state (the state shown in FIG. 12), the endoscope body 1 and the first holding tray 25 are stored in the sterilizing package 22.

The sterilizing package 22 has the opening portion 22*a* closed by the fastener 22*b*. Consequently, the sterilizing package 22 is sealed internally. This state is shown in FIG. 13. In the state shown in FIG. 13, a predetermined sterilization process (e.g., ethylene oxide gas sterilization process) is performed with respect to the endoscope 100C.

Figure 14:
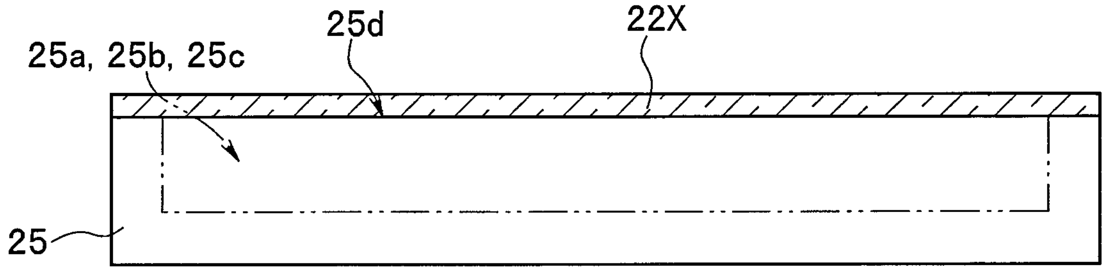
FIG. 14 is a side view showing a side face of a first holding tray according to a modification of the fourth embodiment of the present disclosure.

Regarding the endoscope according to the fourth embodiment described above, a modification such as shown below is conceivable. FIG. 14 is a diagram showing a modification of the fourth embodiment of the present disclosure. FIG. 14 is a side view of a first holding tray according to the present modification, i.e., a side face seen in the direction of the arrow [14] in FIG. 12.

The present modification adopts a configuration in which instead of the sterilizing package 22 (see FIG. 13) according to the fourth embodiment described above, a sterilizing sheet 22X is pasted to the flat surface 25*d* of the first holding tray 25 as shown in FIG. 14.

The sterilizing sheet 22X, which is pervious to sterilizing gas such as ethylene oxide gas, is produced using a publicly-known sheet-like member made of a material substantially the same as the sterilizing package 22 described above.

Such a configuration allows the sterilizing sheet 22X to seal the multiple housing grooves (25*a*, 25*b*, and 25*c*).

The configuration of the present modification allows the first holding tray 25 and the sterilizing sheet 22X to also serve as a container for use to hold the endoscope body 1 and a sterilizing package without preparing the sterilizing package 22 separately.

As described above, the fourth embodiment can achieve effects substantially the same as the first embodiment described above. Besides, according to the present embodiment, the first holding tray 25 serving as a holding member is of a tray form provided with the contiguous housing grooves (25*a*, 25*b*, and 25*c*) capable of housing the endoscope body 1, and thus can house the endoscope body 1 more easily than the holding member of a sheath form according to the first to third embodiments described above. This contributes to improvement of working efficiency prior to the sterilization process.

Figure 15:
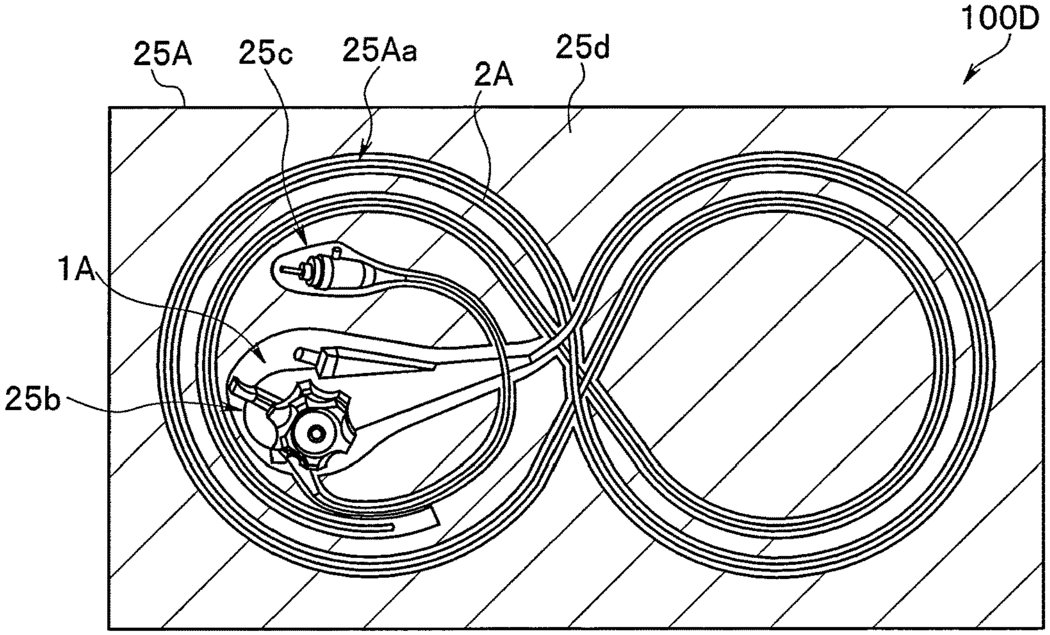
FIG. 15 is a conceptual diagram showing how an endoscope body of an endoscope according to a fifth embodiment of the present disclosure is housed in a second holding tray.
Figure 16:
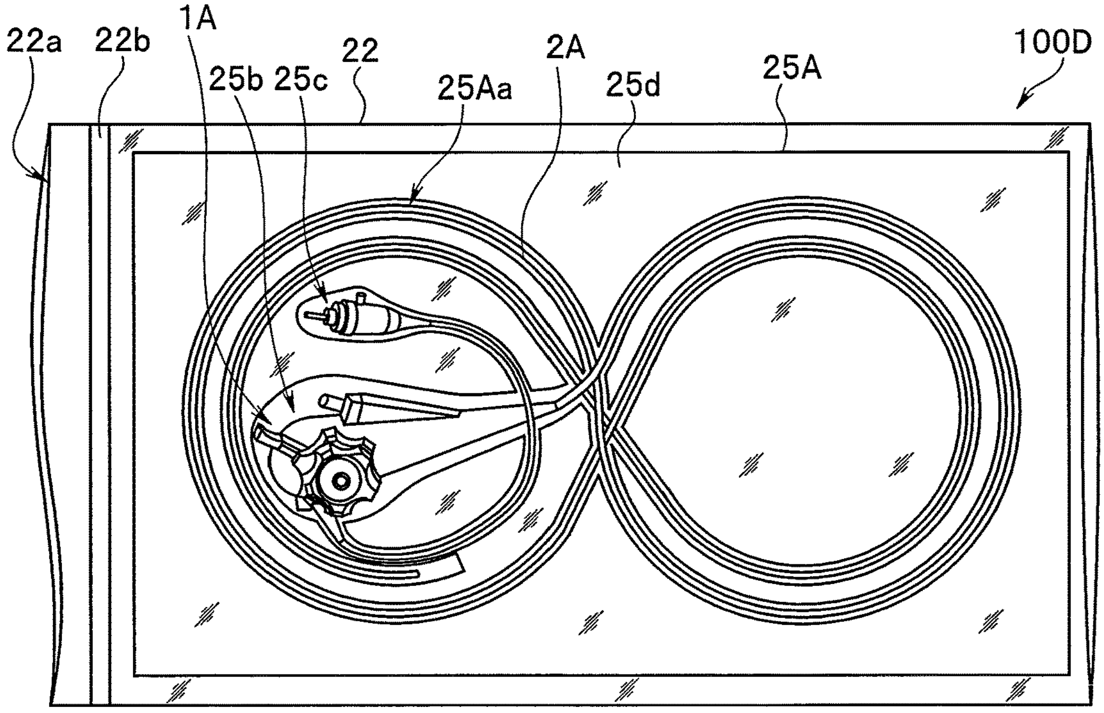
FIG. 16 is a conceptual diagram showing how the endoscope of FIG. 15 is stored in a sterilizing package.

Next, an endoscope according to a fifth embodiment of the present disclosure will be described below using FIGS. 15 and 16. FIGS. 15 and 16 are diagrams showing the endoscope according to the fifth embodiment of the present disclosure, of which FIG. 15 is a conceptual diagram showing how an endoscope body of an endoscope according to a fifth embodiment of the present disclosure is housed in a second holding tray; and FIG. 16 is a conceptual diagram showing how the endoscope of FIG. 15 is stored in a sterilizing package.

Basic configuration of the present embodiment is substantially the same as the fourth embodiment described above. In the present embodiment, a configuration of a holding member (a second holding tray 25A) differs from the configuration of the fourth embodiment (the first holding tray 25). Thus, in the present embodiment, description of the same members as the fourth embodiment is omitted, and only different part will be described in detail below.

An endoscope 100D according to the present embodiment includes the endoscope body 1A and the second holding tray 25A as shown in FIG. 15.

The endoscope body 1A is the same as the endoscope body 1A applied in the second embodiment described above. The endoscope body 1A includes a longer and flexible insertion portion 2A. The configuration of the endoscope body 1A itself is as described above (see FIGS. 1 and 2).

The second holding tray 25A is a holding member for use to hold the endoscope body 1A including the insertion portion 2A in a predetermined shape. The second holding tray 25A is a container having a cavity capable of housing the endoscope body 1A.

Therefore, the second holding tray 25A includes an insertion portion housing groove 25Aa, the operation portion housing groove 25*b*, and the connector housing groove 25*c*, of which the operation portion housing groove 25*b* and the connector housing groove 25*c* are substantially the same as the first holding tray 25 according to the fourth embodiment described above.

The insertion portion housing groove 25Aa is formed in a concave groove shape that can house substantially an entire area of the insertion portion 2A from the distal end to near the proximal end by maintaining a predetermined shape. Of the second holding tray 25A, which is a holding member illustrated by example in the present embodiment, the insertion portion housing groove 25Aa forms a plurality of substantially 8-like shapes on the same plane, as shown in FIG. 15.

The second holding tray 25A configured as described above is the same as the holding members of other embodiments described above in being formed to have at least two different winding directions and formed as a holding member, part of which is substantially S-shaped.

The endoscope 100D according to the present embodiment further includes the sterilizing package 22 as shown in FIG. 16. The sterilizing package 22 is a packaging material capable of housing the endoscope body 1A and the second holding tray 25A (a holding member), and is a package of the same bag-like form as the package shown in the first embodiment described above.

As shown in FIG. 16, the sterilizing package 22 also has a size that allows the second holding tray 25A to be stored with the endoscope body 1A being stored in the second holding tray 25A. Thus, the sterilizing package 22 can store the second holding tray 25A with the predetermined shape (substantially an 8-like shape) of the insertion portion 2A being maintained.

Working of the endoscope 100D according to the fifth embodiment configured as described above is substantially the same as the fourth embodiment described above. The fifth embodiment can accommodate even the endoscope body 1A equipped with the long insertion portion 2A and achieve effects exactly the same as the fourth embodiment.

Figure 17:
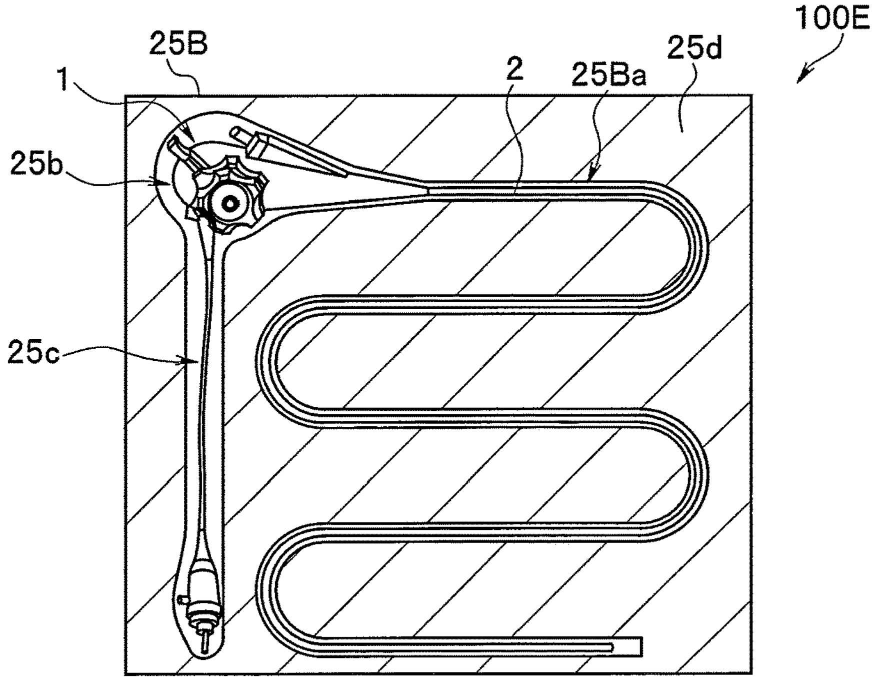
FIG. 17 is a conceptual diagram showing how an endoscope body of an endoscope according to a sixth embodiment of the present disclosure is housed in a third holding tray.
Figure 18:
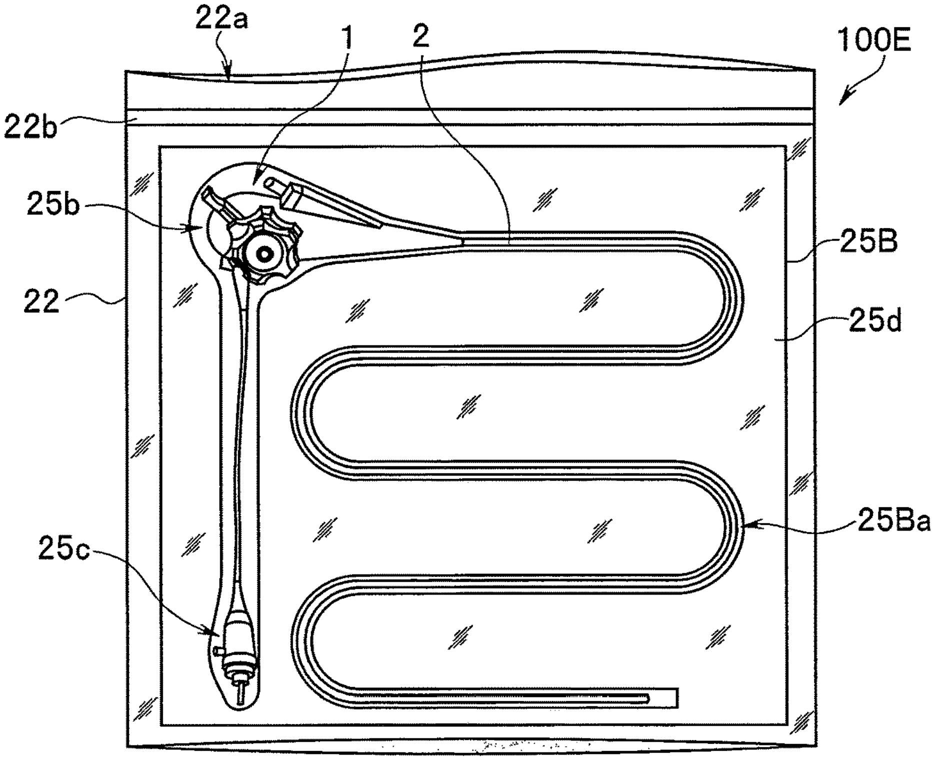
FIG. 18 is a conceptual diagram showing how the endoscope of FIG. 17 is stored in a sterilizing package.

Next, an endoscope according to a sixth embodiment of the present disclosure will be described below using FIGS. 17 and 18. FIGS. 17 and 18 are diagrams showing the endoscope according to the sixth embodiment of the present disclosure, of which FIG. 17 is a conceptual diagram showing how an endoscope body of the endoscope according to the sixth embodiment of the present disclosure is housed in a third holding tray; and FIG. 18 is a conceptual diagram showing how the endoscope of FIG. 17 is stored in a sterilizing package.

Basic configuration of the present embodiment is substantially the same as the fourth embodiment described above. In the present embodiment, a configuration of a holding member (a third holding tray 25B) differs from the configuration of the fourth embodiment (the first holding tray 25). Thus, in the present embodiment, description of the same members as the fourth embodiment is omitted, and only different part will be described in detail below.

An endoscope 100E according to the present embodiment includes the endoscope body 1 and the third holding tray 25B as shown in FIG. 17.

The endoscope body 1 is the same as the endoscope body 1 applied in the fourth embodiment described above. The configuration of the endoscope body 1 itself is as described above (see FIGS. 1 and 2).

The third holding tray 25B is a holding member for use to hold the endoscope body 1. In this case, the third holding tray 25B holds the insertion portion 2 in a predetermined shape. The third holding tray 25B is a container having a cavity capable of housing the endoscope body 1.

Therefore, the third holding tray 25B includes an insertion portion housing groove 25Ba, the operation portion housing groove 25*b*, and the connector housing groove 25*c*, of which the operation portion housing groove 25*b* and the connector housing groove 25*c* have functions which, although different in shape, are substantially the same as the respective housing grooves (25*b* and 25*c*) of the first holding tray 25 according to the fourth embodiment described above.

The insertion portion housing groove 25Ba is formed in a concave groove shape that can house substantially an entire area of the insertion portion 2 from the distal end to near the proximal end by maintaining a predetermined shape. Of the third holding tray 25B, which is a holding member illustrated by example in the present embodiment, the insertion portion housing groove 25Ba is substantially wave-shaped or meander-shaped as a whole as shown in FIG. 17.

The third holding tray 25B configured as described above is the same as the holding members of other embodiments described above in being formed to have at least two different winding directions and formed as a holding member, part of which is substantially S-shaped.

The endoscope 100E according to the present embodiment further includes the sterilizing package 22 as shown in FIG. 18. The sterilizing package 22 is a packaging material capable of housing the endoscope body 1 and the third holding tray 25B (a holding member), and is a package of the same bag-like form as the package shown in the first embodiment described above.

As shown in FIG. 18, the sterilizing package 22 also has a size that allows the third holding tray 25B to be stored with the endoscope body 1 being stored in the third holding tray 25B. Thus, the sterilizing package 22 can store the third holding tray 25B with the predetermined shape (substantially a wave shape or a meander shape) of the insertion portion 2 being maintained.

Working of the endoscope 100E according to the sixth embodiment configured as described above is substantially the same as the fourth embodiment described above. The sixth embodiment can achieve effects exactly the same as the fourth embodiment.

Figure 19:
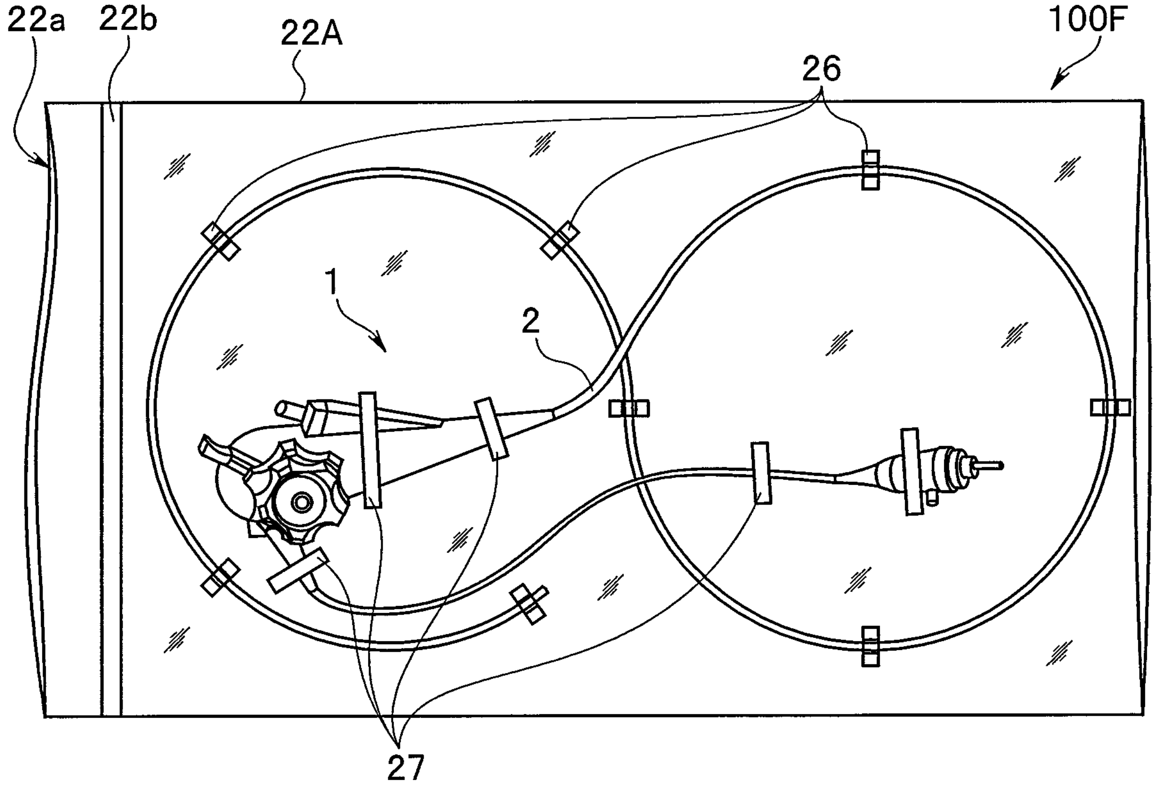
FIG. 19 is a conceptual diagram showing how an endoscope body of an endoscope according to a seventh embodiment of the present disclosure is held by being stored in a second sterilizing package.
Figure 20:
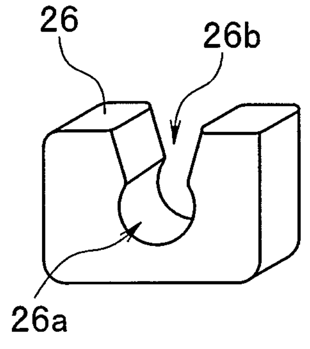
FIG. 20 is an external perspective view of an insertion portion fixing member picked out solely from the endoscope of FIG. 19 and shown in an enlarged form.
Figure 21:
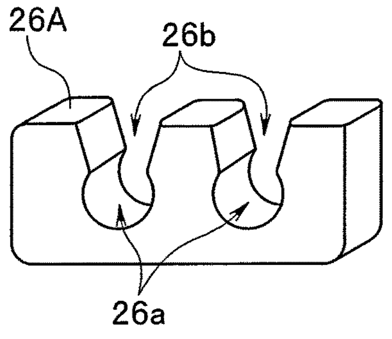
FIG. 21 is an external perspective view showing a modification of the insertion portion fixing member of FIG. 20.

Next, an endoscope according to a seventh embodiment of the present disclosure will be described below using FIGS. 19 to 21. FIGS. 19 to 21 are diagrams showing the endoscope according to the seventh embodiment of the present disclosure, of which FIG. 19 is a conceptual diagram showing how an endoscope body of an endoscope according to the seventh embodiment of the present disclosure is held by being stored in a second sterilizing package; FIG. 20 is an external perspective view of an insertion portion fixing member picked out solely from the endoscope of FIG. 19 and shown in an enlarged form; and FIG. 21 is an external perspective view showing a modification of the insertion portion fixing member of FIG. 20.

Basic configuration of the present embodiment is substantially the same as the first embodiment described above. The present embodiment differs from the first embodiment in the form of a holding member. The holding member according to the present embodiment differs in that a second sterilizing package 22A is applied instead of the first holding sheath 21 according to the first embodiment. Thus, in the present embodiment, description of the same members as the first embodiment is omitted, and only different part will be described in detail below.

An endoscope 100F according to the present embodiment includes the endoscope body 1 and the second sterilizing package 22A as shown in FIG. 19.

The endoscope body 1 is the same as the endoscope body 1 applied in the first embodiment described above. The configuration of the endoscope body 1 itself is as described above (see FIGS. 1 and 2).

The second sterilizing package 22A is a holding member for use to house and hold the endoscope body 1. In this case, the second sterilizing package 22A is a packaging material configured to hold the insertion portion 2 in a predetermined shape. Basic configuration of the second sterilizing package 22A is a package of a bag-like form substantially the same as the package shown in the first embodiment described above.

As shown in FIG. 19, the second sterilizing package 22A is configured to maintain the predetermined shape (substantially an S-like shape) of the insertion portion 2 with the endoscope body 1 being stored. For that, a plurality of insertion portion fixing members 26 are provided at respective predetermined positions on an inner surface of the second sterilizing package 22A. Two interior surfaces of the second sterilizing package 22A are adhered to each other to form a track.

As shown in FIG. 20, each of the insertion portion fixing members 26 is block-shaped as a whole, and includes a through-hole 26*a* that allows passage of the insertion portion 2, and an opening 26*b* connected to the through-hole 26*a*. The insertion portion 2 is inserted into the insertion portion fixing member 26 through the opening 26*b* and placed in the through-hole 26*a*. Consequently, the insertion portion 2 can be fixed to the insertion portion fixing member 26. By being fixed to the insertion portion fixing members 26, the insertion portion 2 is positioned at a predetermined location in the second sterilizing package 22A.

Therefore, the plurality of insertion portion fixing members 26 are placed at predetermined positions in the second sterilizing package 22A such that the insertion portion 2 will assume a predetermined shape. In the present embodiment, a form in which the predetermined shape of the insertion portion 2 is substantially an S-like shape is illustrated by example.

Consequently, as shown in FIG. 19, the insertion portion 2 stored in the second sterilizing package 22A assumes substantially an S-like shape.

Note that in the second sterilizing package 22A, which is the holding member according to the present embodiment, as shown in FIG. 20, apart from the insertion portion fixing members 26, fixing members 27 are provided to fix the operation portion 3, the scope connector 16, the universal cable 4, and the like. Although detailed illustration is omitted, the fixing members 27 can be formed, for example, into a substantially same shape as the insertion portion fixing members 26.

In the case of the endoscope 100F according to the present embodiment configured as described above, before a sterilization process is performed, the endoscope body 1 is stored in the second sterilizing package 22A, the insertion portion 2 is fixed by the plurality of insertion portion fixing members 26, and the operation portion 3, the scope connector 16, the universal cable 4, and the like are fixed by the fixing members 27 (the state shown in FIG. 19).

Then, the opening portion 22*a* of the second sterilizing package 22A is closed by the fastener 22*b*. Consequently, the second sterilizing package 22A is sealed internally. This state is shown in FIG. 19. In the state shown in FIG. 19, a predetermined sterilization process (e.g., ethylene oxide gas sterilization process) is performed with respect to the endoscope 100F.

As described above, the seventh embodiment can achieve effects substantially the same as the first embodiment described above. In the present embodiment, the second sterilizing package 22A serving as a holding member is in a bag-like form, and thus can simplify component members compared to the holding member of a sheath form according to the first to third embodiments described above or the holding member of a tray form according to the fourth to sixth embodiments described above. Besides, the present embodiment makes it easier to house the endoscope body 1 in the second sterilizing package 22A of a bag form. This contributes to improvement of working efficiency prior to the sterilization process.

Note that in the form illustrated above by example in the seventh embodiment, the predetermined shape of the insertion portion 2 with the endoscope body 1 being stored in the second sterilizing package 22A is substantially an S-like shape. However, in addition to the configuration example described above, the present embodiment can adopt another form regarding the shape of the insertion portion 2.

For example, as the predetermined shape of the insertion portion 2 with the endoscope body 1 being stored in the sterilizing package, substantially an 8-like shape illustrated by example in the second and fifth embodiments described above (see FIGS. 5, 12, and the like) may be adopted.

In that case, for example, an insertion portion fixing member 26A of a form such as shown in FIG. 21 can be used. As shown in FIG. 21, in the insertion portion fixing member 26A, pairs of through-holes 26*a* and openings 26*b* are formed side by side in two adjacent locations, respectively. By using a plurality of the insertion portion fixing members 26A of such a form, the insertion portion 2 can be fixed in the second sterilizing package 22A while maintaining substantially an 8-like shape.

Such a modification can also achieve effects substantially the same as the seventh embodiment described above.

Figure 22:
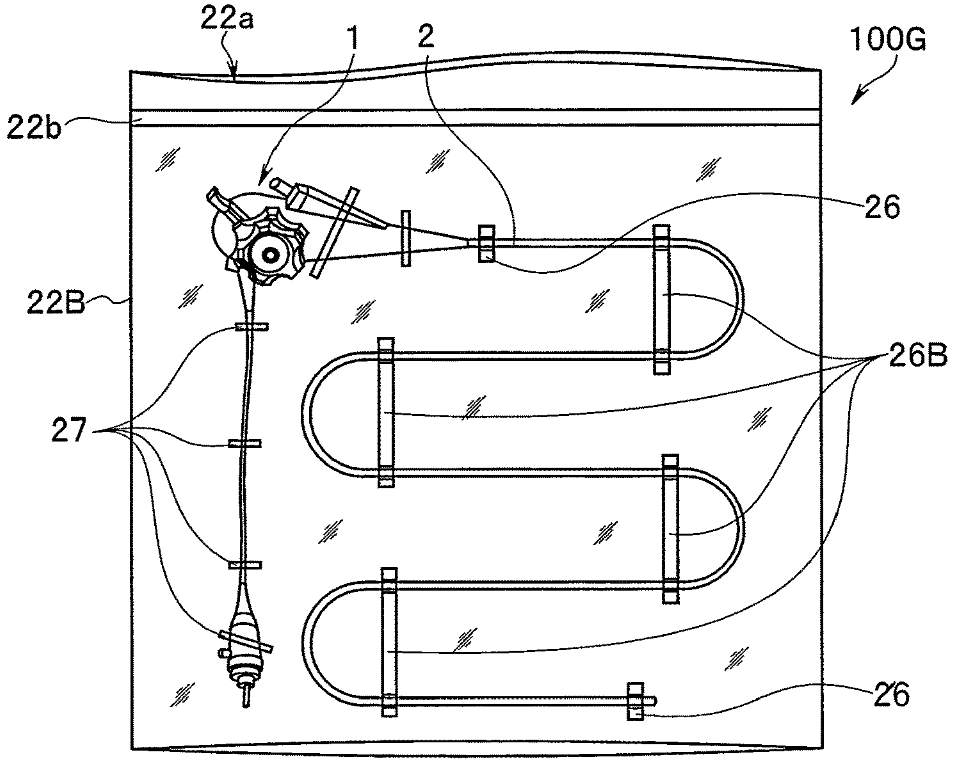
FIG. 22 is a conceptual diagram showing how an endoscope body of an endoscope according to an eighth embodiment of the present disclosure is held by being stored in a third sterilizing package.
Figure 23:
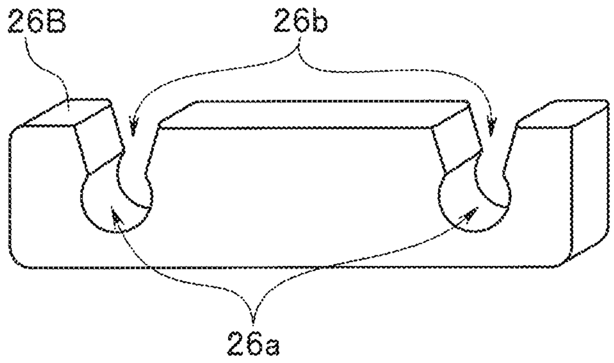
FIG. 23 is an external perspective view of a second insertion portion fixing member picked out solely from the endoscope of FIG. 22 and shown in an enlarged form.

Next, an endoscope according to an eighth embodiment of the present disclosure will be described below using FIGS. 22 and 23. FIGS. 22 and 23 are diagrams showing the endoscope according to the eighth embodiment of the present disclosure, of which FIG. 22 is a conceptual diagram showing how an endoscope body of the endoscope according to an eighth embodiment of the present disclosure is held by being stored in a third sterilizing package; and FIG. 23 is an external perspective view of a second insertion portion fixing member picked out solely from the endoscope of FIG. 22 and shown in an enlarged form.

Basic configuration of the present embodiment is substantially the same as the seventh embodiment described above. In the present embodiment, a configuration of a holding member (a third sterilizing package 22B) differs from the configuration of the seventh embodiment (the second sterilizing package 22A). Thus, in the present embodiment, description of the same members as the seventh embodiment is omitted, and only different part will be described in detail below.

An endoscope 100G according to the present embodiment includes the endoscope body 1 and the third sterilizing package 22B as shown in FIG. 22.

The endoscope body 1 is the same as the endoscope body 1 applied in the first embodiment described above. The configuration of the endoscope body 1 itself is as described above (see FIGS. 1 and 2).

The third sterilizing package 22B is a holding member for use to house and hold the endoscope body 1. In this case, as shown in FIG. 22, the third sterilizing package 22B is configured to maintain the predetermined shape (substantially a wave shape or a meander shape) of the insertion portion 2 with the endoscope body 1 being stored. For that, a plurality of insertion portion fixing members 26 and 26B are provided at respective predetermined positions on an inner surface of the third sterilizing package 22B.

The insertion portion fixing member 26 here is the same as the insertion portion fixing member 26 used in the seventh embodiment described above (see FIG. 20). As shown in FIG. 22, basically the insertion portion fixing member 26B is substantially the same as the insertion portion fixing members 26 and 26A described above. The insertion portion fixing member 26B differs from the insertion portion fixing member 26A (see FIG. 21) in that the pairs of through-holes 26*a* and openings 26*b* are formed at locations a predetermined distance away from each other.

The use of the insertion portion fixing member 26B allows the third sterilizing package 22B to fix the insertion portion 2 with substantially a wave shape or a meander shape maintained in the second sterilizing package 22A.

Working of the endoscope 100G according to the eighth embodiment configured as described above is substantially the same as the seventh embodiment described above. The eighth embodiment can achieve effects exactly the same as the seventh embodiment.

Incidentally, a long conduit, bending wires, a signal line, and the like pass inside an insertion portion of conventional endoscopes. Of such long structures, the plurality of bending wires are placed advanceably/retractably in a major axis direction of the insertion portion. It is advisable to place the plurality of bending wires in a region close to an outer periphery of the insertion portion.

On the one hand, of the long structures passing through the insertion portion, it is advisable that the treatment instrument passage conduit, which has a relatively large diameter, be placed near an axial center portion of the insertion portion to avoid interference with the plurality of bending wires placed toward the outer periphery of the insertion portion.

On the other hand, an image pickup unit, an illumination unit, and the like are disposed inside a distal end portion of the insertion portion. Therefore, it is recommended that in the distal end portion, the treatment instrument passage conduit be placed in a region close to the outer periphery of the insertion portion to avoid interference with the image pickup unit, the illumination unit, and the like. Consequently, a distal end opening of the treatment instrument passage conduit is placed in the region close to the outer periphery of the distal end portion.

To implement such a configuration, there are cases in which the treatment instrument passage conduits in conventional endoscopes are formed by shifting position within the insertion portion in a direction orthogonal to the axis direction of the insertion portion between internal placement up to the bending portion and internal placement of the distal end portion.

Figure 24:
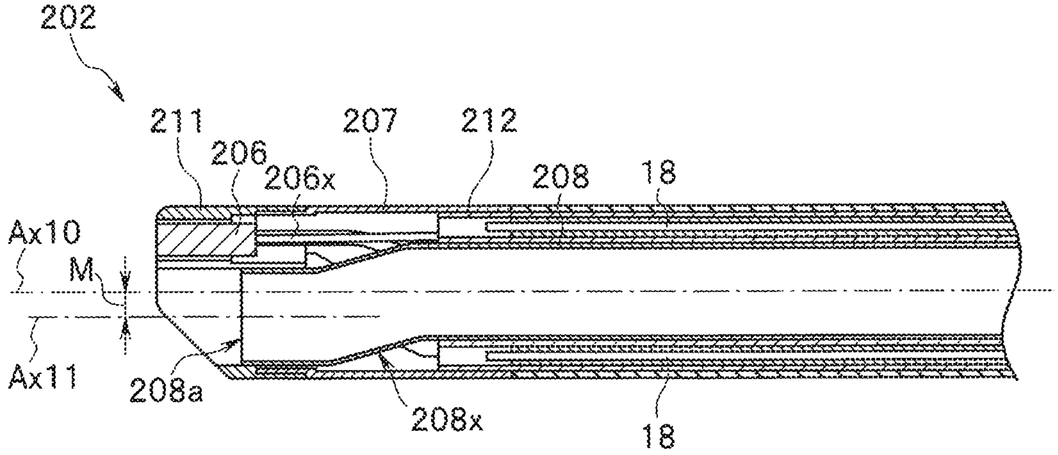
FIG. 24 (PRIOR ART)
FIG. 24 is a schematic sectional view showing a configuration in the vicinity of a distal end portion of an insertion portion of a conventional endoscope.

For example, FIG. 24 is a schematic diagram showing a configuration in the vicinity of a distal end portion of an insertion portion of a conventional endoscope. A cross section along a central axis of the insertion portion is shown in FIG. 24. Note that in FIG. 24, reference sign Ax10 denotes the central axis of the insertion portion.

The conventional endoscope 202 shown in FIG. 24 includes a distal end portion 211, a connection ring 207, and a bending portion 212, which are connected in a row starting from the distal end side.

An image pickup unit 206 is disposed in the distal end portion 211. A signal line 206*x* extends toward the proximal end side from the image pickup unit 206. The signal line 206*x* passes inside the distal end portion 211, the connection ring 207, and the bending portion 212.

Note that various types of other component members are disposed in the distal end portion 211, but illustration of the other component members is omitted to avoid complicating the drawing in FIG. 24.

A treatment instrument passage conduit 208 is passed through the insertion portion of the endoscope 202. In this case, part of the treatment instrument passage conduit 208 on the distal end side is disposed in the distal end portion 211. Inside the bending portion 212, the treatment instrument passage conduit 208 is disposed near the axial center portion of the insertion portion.

Inside the distal end portion 211, a distal end opening 208*a* of the treatment instrument passage conduit 208 is placed in a position close to an outer periphery where interference with the image pickup unit 206 does not occur. Here, reference sign Ax11 in FIG. 24 denotes a central axis of the distal end opening 208*a*.

The connection ring 207 is a connecting member configured to connect the distal end portion 211 and the bending portion 212. The signal line 206*x* of the image pickup unit 206 and part of the treatment instrument passage conduit 208 on the distal end side are disposed inside the connection ring 207.

A bent portion 208*x* created by bending the treatment instrument passage conduit 208 is disposed in the connection ring 207. The bent portion 208*x* is a part formed to offset the distal end opening 208*a* from the treatment instrument passage conduit 208 in a cross section of the insertion portion. In the example shown in FIG. 24, the distal end opening 208*a* is offset in the cross section of the insertion portion by a distance indicated by reference sign M.

In other words, the bent portion 208*x* causes the distal end opening 208*a* of the treatment instrument passage conduit 208 to be placed toward the outer periphery inside the distal end portion 211. The bent portion 208*x* also causes the treatment instrument passage conduit 208 to be placed near the axial center portion of the insertion portion in an inner region (excluding the distal end portion 211) closer to the proximal end than is the bending portion 212. In other words, for example, a central axis of the treatment instrument passage conduit 208 is placed by being substantially aligned with the central axis Ax10 of the insertion portion.

The plurality of bending wires 18 are placed inside the bending portion 212. Inside the bending portion 212, the plurality of bending wires 18 are placed in a region close to the outer periphery of the distal end portion.

In this way, the treatment instrument passage conduit 208 in some conventional endoscopes 202 include the bent portion 208*x* provided inside a connection region (the connection ring 207) between the bending portion 212 and the distal end portion 211.

With such a configuration, the treatment instrument passage conduit 208 is structured such that the central axis Ax10 in an inner region closer to the proximal end than is the bending portion 212 and the central axis Ax11 of the distal end opening 208*a* will be offset from each other by the predetermined distance M in a cross section orthogonal to a longitudinal axis of the insertion portion (see FIG. 24).

On the other hand, regarding conventional endoscopes of another form, for example, as a simple and easy configuration intended to implement a flexible insertion portion having flexibility, an endoscope of a form that uses a so-called multi lumen tube (hereinafter abbreviated to MLT) has been put to practical use.

In an endoscope, the insertion portion of which is made up of an MLT, various types of conduits (such as the treatment instrument passage conduit) can be passed through the insertion portion using lumens in the MLT.

However, in the endoscope that adopts an insertion portion made up of an MLT, in order to implement a configuration in which there is an offset in the internal placement of the treatment instrument passage conduit between placement of the treatment instrument passage conduit on the proximal end side (around the center of the bending portion) and placement of the distal end opening (close to an outer periphery of the distal end portion) as described above, a connecting tube is supposed to be put between the distal end portion and the MLT.

Figure 25:
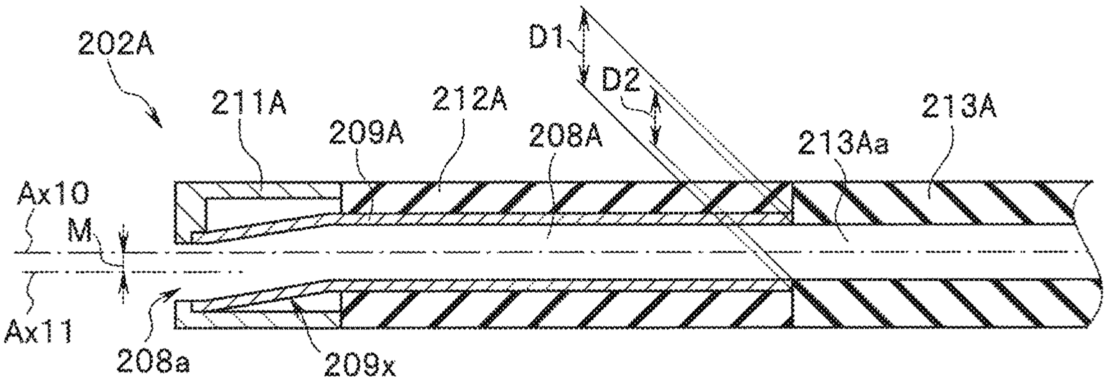
FIG. 25 (PRIOR ART)
FIG. 25 is a sectional view conceptually showing a configuration in the vicinity of a distal end portion of an insertion portion that uses an MLT in a conventional endoscope.

For example, FIG. 25 is a diagram conceptually showing a configuration in the vicinity of a distal end portion of an insertion portion of an endoscope of a conventional form that adopts an insertion portion using an MLT. Note that FIG. 25 shows a cross section along the central axis of the insertion portion. FIG. 25 shows only major component members by omitting detailed illustration of internal component members.

The conventional endoscope 202A shown in FIG. 25 includes a distal end portion 211A, a first MLT 212A, and a second MLT 213A, which are connected in a row starting from the distal end side. Here, the first MLT 212A is slightly more flexible than the second MLT 213A. Consequently, the first MLT 212A functions as a bending portion.

A connecting tube 209A is placed in the first MLT 212A, passing through the first MLT 212A. The connecting tube 209A is connected by extending to a treatment instrument passage conduit 208A made up of a main lumen 213Aa of the second MLT 213A.

On the distal end side, the connecting tube 209A is placed inside the distal end portion 211A. In this case, the connecting tube 209A has a bent portion 209*x* inside the distal end portion 211A. On the distal end side, an opening is formed in the bent portion 209*x* of the connecting tube 209A as the distal end opening 208*a* of the treatment instrument passage conduit 208A.

With such a configuration, in the bent portion 209*x* of the connecting tube 209A, the distal end opening 208*a* is placed in a position close to an outer periphery in an inner region of the distal end portion 211A by avoiding interference with internal structures (not illustrated) such as an image pickup unit provided inside the distal end portion 211A.

In so doing, the treatment instrument passage conduit 208A is placed near the axial center portion in an inner region closer to the proximal end than is the first MLT 212A, and the distal end opening 208*a* is placed toward an outer periphery of the distal end portion 211A. Consequently, the central axis Ax10 of the treatment instrument passage conduit 208A and the central axis Ax11 of the distal end opening 208*a* are placed by being offset from each other by the predetermined distance M in a cross section orthogonal to the longitudinal axis of the insertion portion (see FIG. 25).

In this way, in the conventional endoscope that adopts an insertion portion using an MLT, in order to offset the distal end opening toward the outer periphery of the distal end portion, a connecting tube is used, resulting in the use of an increased number of parts.

The use of a connecting tube poses a problem in that outer diameter of the insertion portion is increased by the wall thickness of the connecting tube. If a configuration that will curb increases in the outer diameter of the insertion portion is adopted by taking the above problem into consideration, reduction in inner diameter of the treatment instrument passage conduit will pose a problem.

If the connecting tube 209A is provided to fit inner diameter (reference sign D2 in FIG. 25) of the main lumen 213Aa of the second MLT 213A, for example, as shown in FIG. 25, the outer diameter of the insertion portion is increased by the wall thickness (outer diameter D1−inner diameter D2) of the connecting tube 209A.

Thus, regarding an endoscope, the insertion portion of which is formed of an MLT, using FIG. 26, description will be given below of a more optimal configuration example for implementing a configuration in which a central axis of a treatment instrument passage conduit placed toward a proximal end of the insertion portion and a central axis of the distal end opening placed in a distal end portion are placed by being offset from each other in a cross section orthogonal to the longitudinal axis of the insertion portion.

Figure 26:
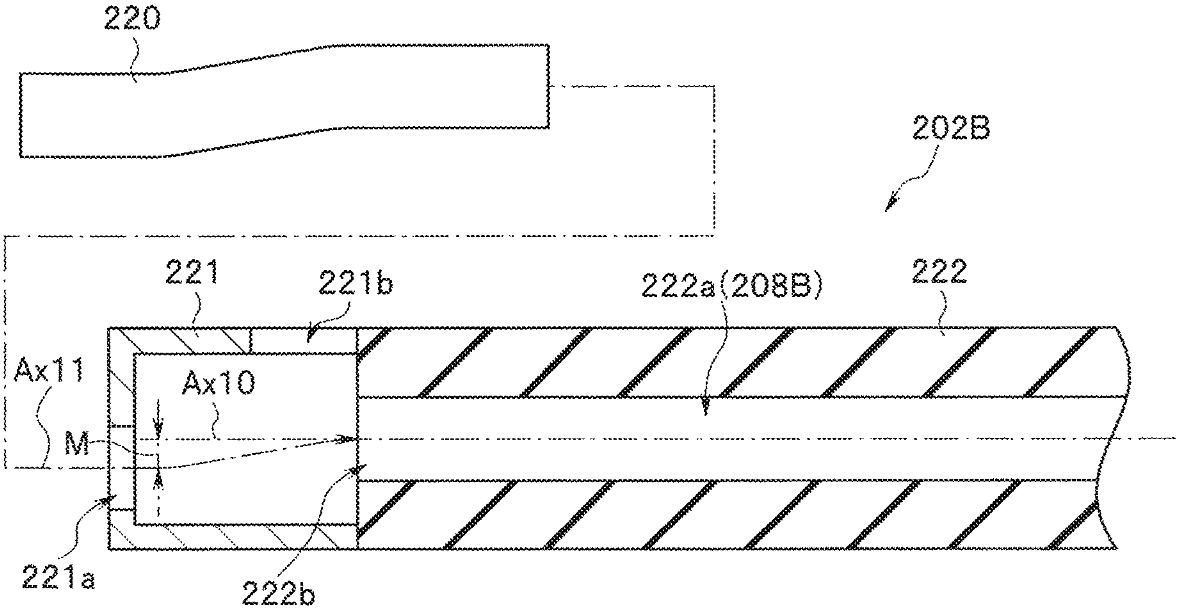
FIG. 26 is a diagram conceptually showing an endoscope according to one configuration example.

FIG. 26 is a diagram conceptually showing an endoscope according to one configuration example. FIG. 26 conceptually shows only a basic configuration of the endoscope.

An insertion portion of the endoscope 202B according to the configuration example shown in FIG. 26 includes a distal end portion 221 and an MLT 222. A distal end opening 221*a* with a central axis Ax11 is formed in the distal end portion 221. The distal end opening 221*a* is formed at a position offset from a central axis Ax10 of the insertion portion by a predetermined distance M in a cross section orthogonal to a longitudinal axis of the insertion portion.

A through-hole 221*b* is formed in part of a side face of the distal end portion 221. The through-hole 221*b* penetrates the side face of the distal end portion 221, causing the outside and inside of the side wall to communicate with each other.

The MLT 222 is connected to a proximal end side of the distal end portion 221. A main lumen 222*a* is formed in the MLT 222 with a central axis substantially aligned with the central axis Ax10. The main lumen 222*a* corresponds to a treatment instrument passage conduit 208B.

In the case of the endoscope 202B according to the present configuration example configured as described above, part of the treatment instrument passage conduit 208B on the distal end side is formed in a predetermined area inside the distal end portion 221 using a conduit formation jig 220 of a form such as shown in FIG. 26.

For that, the conduit formation jig 220 is removably disposed between the distal end opening 221*a* and a lumen opening 222*b*. The conduit formation jig 220 is formed of a material having flexibility.

Next, working of forming part of the treatment instrument passage conduit 208B on the distal end side inside the distal end portion 221 of the endoscope 202B according to the present configuration example using the conduit formation jig 220 will be described below briefly using FIG. 27.

First, as shown in FIG. 26, the endoscope 202B according to the present configuration example has a form in which the distal end portion 221 and the MLT 222 are connected. With the endoscope 202B being placed in this state, as shown in [27A] of FIG. 27, the conduit formation jig 220 inserted from the distal end opening 221*a* in the distal end portion 221 is inserted into the lumen opening 222*b* on the distal end side of the main lumen 222*a* of the MLT 222. Consequently, the conduit formation jig 220 is placed between the distal end opening 221*a* and the lumen opening 222*b*.

In this case, the central axis Ax11 of the distal end opening 221*a* and the central axis Ax10 of the lumen opening 222*b* are formed at positions offset from each other by the distance M shown in FIG. 26 in a cross section orthogonal to the longitudinal axis of the insertion portion as described above.

Figure 27:
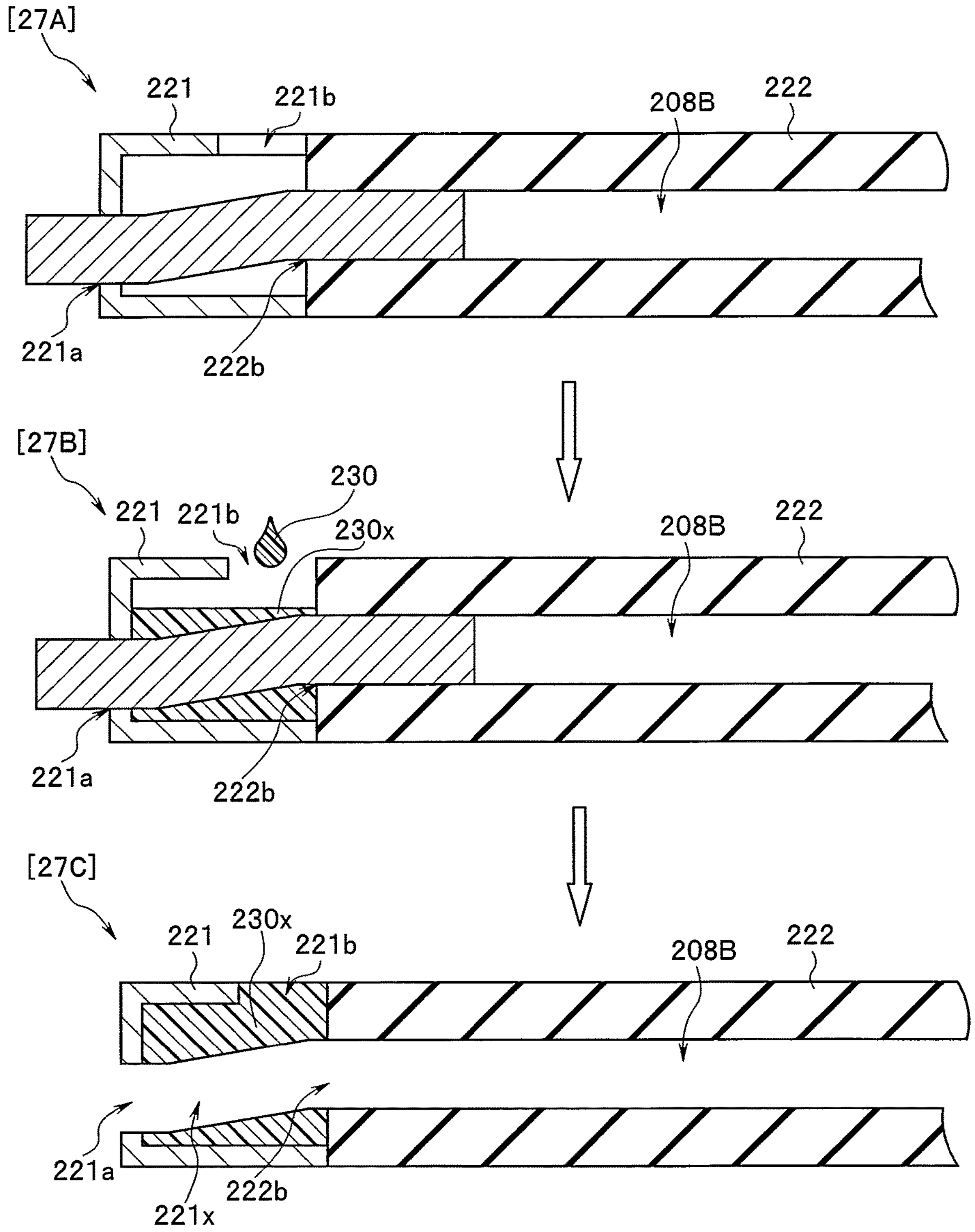
FIG. 27 is a diagram showing working of forming part of a treatment instrument passage conduit on a distal end side inside a distal end of the endoscope according to the configuration example of FIG. 26 using a conduit formation jig.

Therefore, at this time, the conduit formation jig 220 is bent into a predetermined form inside the distal end portion 221 as shown in [27A] of FIG. 27. Then, the bent form of the conduit formation jig 220 is maintained.

In this state, as shown in [27B] of FIG. 27, a predetermined adhesive 230 is poured into the through-hole 221*b* in the distal end portion 221. Soon, the adhesive 230 is filled into the distal end portion 221.

Subsequently, before the adhesive 230 has cured, the conduit formation jig 220 is pulled out. Then, as shown in [27C] of FIG. 27, a bent conduit 221*x* having a bent portion is formed between the distal end opening 221*a* and the lumen opening 222*b* inside the distal end portion 221. Then, when the adhesive 230 has cured, it becomes possible to use the bent conduit 221*x* as part of the treatment instrument passage conduit 208B without problems.

As described above, with the endoscope 202B according to the configuration example, the conduit formation jig 220 and the adhesive 230 allow the bent conduit 221*x* to be formed easily in the distal end portion 221.

Therefore, in an endoscope in which the insertion portion is formed using an MLT, a configuration in which the central axis of the distal end opening 221*a* and the central axis of the lumen opening 222*b* are placed by being offset from each other in a cross section orthogonal to the longitudinal axis of the insertion portion can be implemented easily by a simple operation process without increasing the number of parts.

Furthermore, since a connecting tube is not used, the inner diameter of the treatment instrument passage conduit can be kept to an appropriate size without increasing the outer diameter of the insertion portion.

The present disclosure is not limited to the embodiments described above and needless to say, various alterations and applications are possible without departing from the gist of the disclosure. Furthermore, the embodiments described above include disclosures at various stages, and various disclosures can be extracted through appropriate combinations of the disclosed components. For example, even if some of the components are removed from any of the embodiments described above, the resulting configuration can be extracted as a form of the present disclosure as long as the configuration can solve the problems to be solved by the disclosure and provide the advantages described above. Furthermore, components may be combined as appropriate across different embodiments. Accordingly, the present disclosure is to be limited only by the appended claims and not by any specific embodiment of the present disclosure.

What is claimed is:

1. An endoscope package system, comprising:

an endoscope including a flexible insertion portion; and a packaging sheath, wherein the flexible insertion portion is located in the packaging sheath, wherein the packaging sheath has a shape that is substantially in the form of an eight and that includes a first winding direction and a second winding direction, wherein the first winding direction is different from the second winding direction, and wherein the packaging sheath has a hardness that maintains the shape.

2. The endoscope package system according to claim 1, wherein the shape includes a first loop formed by the flexible insertion portion extending in the first winding direction, and a second loop formed by the flexible insertion portion extending in the second winding direction, wherein the flexible insertion portion includes a first side surface and a second side surface, the first side surface opposing the second side surface relative to a longitudinal axis of the flexible insertion portion, wherein, in the first loop, the first side surface is on an inner diameter surface of the first loop and the second side surface is on an outer diameter surface of the first loop, and wherein, in the second loop, the second side surface is on an inner diameter surface of the second loop and the first side surface is on an outer diameter surface of the second loop.

3. The endoscope package system according to claim 2, wherein the first winding direction is a clockwise direction, and the second winding direction is a counterclockwise direction.

4. The endoscope package system according to claim 2, wherein a sum of a length of the inner diameter surface of the first loop and a length of the outer diameter surface of the second loop defines a first total length, wherein a sum of a length of the outer diameter surface of the first loop and a length of the inner diameter surface of the second loop defines a second total length, and wherein the first total length equals the second total length.

5. The endoscope package system according to claim 2, wherein the flexible insertion portion further includes:

a first wire extending from a proximal end to a distal end of the flexible insertion portion within the first side surface, and a second wire extending from the proximal end to the distal end of the flexible insertion portion within the second side surface.

6. The endoscope package system according to claim 5, wherein, with the flexible insertion portion arranged in the shape, the first wire has a first length and the second wire has a second length, and the first length equals the second length.

7. The endoscope package system according to claim 1, wherein the endoscope is a single use endoscope.

8. The endoscope package system according to claim 1, wherein the endoscope further includes a bending operation knob configured to move a plurality of wires to bend the flexible insertion portion.

9. The endoscope package system according to claim 1, wherein the shape includes an outer peripheral surface and an inner peripheral surface.

10. The endoscope package system according to claim 9, further comprising a fixing component configured to maintain positions of the outer peripheral surface and the inner peripheral surface to form the shape.

11. The endoscope package system according to claim 9, wherein the shape includes an intersecting portion at which the outer peripheral surface and the inner peripheral surface overlap.

12. The endoscope package system according to claim 1, wherein the packaging sheath is formed of high-impact polystyrene, polyvinyl chloride, or glycol modified polyethylene terephthalate.

* * * * *